(12) United States Patent
Bilder

(10) Patent No.: US 7,015,214 B2
(45) Date of Patent: Mar. 21, 2006

(54) CYANAMIDE, ALKOXYAMINO, AND UREA DERIVATIVES OF 1,3-BENZODIAZEPINE AS HIV REVERSE TRANSCRIPTASE INHIBITORS

(75) Inventor: Donna M Bilder, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 420 days.

(21) Appl. No.: 10/108,842

(22) Filed: Mar. 27, 2002

(65) Prior Publication Data

US 2003/0220327 A1  Nov. 27, 2003

Related U.S. Application Data

(60) Provisional application No. 60/279,217, filed on Mar. 28, 2001.

(51) Int. Cl.
 A61K 31/55 (2006.01)
 A61P 31/18 (2006.01)
 C07D 243/00 (2006.01)

(52) U.S. Cl. .................... 514/220; 514/221; 540/557; 540/567; 540/568

(58) Field of Classification Search ............... 514/220, 514/221; 540/557, 567, 568
 See application file for complete search history.

(56) References Cited

U.S. PATENT DOCUMENTS

| 4,764,512 A | 8/1988 | Molino et al. ............. 214/183 |
| 5,519,021 A | 5/1996 | Young et al. ............. 514/230.5 |
| 5,532,357 A | 7/1996 | Rodgers et al. ............. 540/492 |

FOREIGN PATENT DOCUMENTS

| DE | 4320347 | 12/1994 |
| EP | 0530994 | 8/1992 |
| WO | 93/04047 | 3/1993 |
| WO | 95/12583 | 5/1995 |
| WO | 95/13273 | 5/1995 |
| WO | 00/00479 | 1/2000 |

OTHER PUBLICATIONS

Houpis et al., Synthesis of a New Generation Reverse Transcriptase Inhibitor via the BC 13/GaCl3-Induced Condensation of Anillines with Nitriles (Sugasawa Reaction), Tetrahedron Letters, 1994, pp. 6811-6814, vol. 35, No. 7.

Tucker et al., Synthesis of a Series of 4-(Arylethynyl)-6-Chloro-4-Cyclopropyl-3,4-Dihydroquinazolin-2(1H)-Ones as Novel Non-Nucleoside HIV-1 Reverse Transcriptase Inhibitors, J. Med. Chem., 1994, pp. 2437-2444, vol. 37.

Huffman et al., Lithuum Alkoxides of Cinchona Alkaloids as Chiral Controllers for Enantioselective Acetylide Addition to Cyclic N-Acyl Ketimines, J. Org. Chem., 1995, pp. 1590-1594, vol. 60.

*Primary Examiner*—Brenda Coleman
(74) *Attorney, Agent, or Firm*—Mary K. VanAtten

(57) ABSTRACT

The present invention relates to 1,3-benzodiazepin-2-ones and 1,3-benzoxazepin-2-ones of formula I:

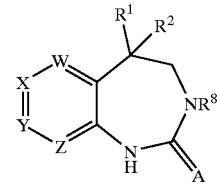

or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

11 Claims, No Drawings

CYANAMIDE, ALKOXYAMINO, AND UREA DERIVATIVES OF 1,3-BENZODIAZEPINE AS HIV REVERSE TRANSCRIPTASE INHIBITORS

CROSS-REFERENCE TO RELATED APPLICATIONS

This application claims the priority benefit of U.S. Application No. 60/279,217, filed on Mar. 28, 2001.

FIELD OF THE INVENTION

This invention relates generally to cyanamide, hydroxyamino, and nitroolefin derivatives of 1,3-benzodiazapines which are useful as inhibitors of HIV reverse transcriptase, pharmaceutical compositions and diagnostic kits comprising the same, methods of using the same for treating viral infection or as assay standards or reagents, and intermediates and processes for making the same.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage.

An active area of research is in the discovery of non-nucleoside HIV reverse transcriptase inhibitors. As an example, it has been found that certain benzoxazinones and quinazolinones are active in the inhibition of HIV reverse transcriptase, the prevention or treatment of infection by HIV and the treatment of AIDS.

U.S. Pat. No. 5,519,021 describe reverse transcriptase inhibitors which are benzoxazinones of the formula:

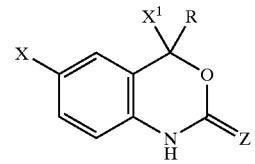

wherein X is a halogen, Z may be O.

EP 0,530,994 and WO 93/04047 describe HIV reverse transcriptase inhibitors which are quinazolinones of the formula A:

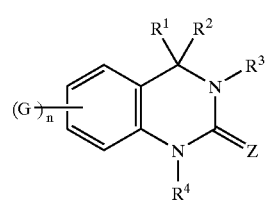

A wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-(−)-6-chloro-4-cyclopropyl-3,4-dihydro-4((2-pyridy)ethynyl)-2(1H)-quinazolinone.

Synthetic procedures for making quinazolinones like those described above are detailed in the following references: Houpis et al, *Tetr. Lett.* 1994, 35(37), 6811–6814; Tucker et al, *J. Med. Chem.* 1994, 37, 2437–2444; and, Huffman et al, *J. Org. Chem.* 1995, 60, 1590–1594.

DE 4,320,347 illustrates quinazolinones of the formula:

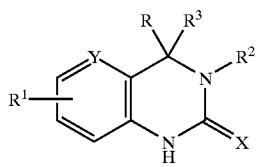

wherein R is a phenyl, carbocyclic ring, or a heterocyclic ring. Compounds of this sort are not considered to be part of the present invention.

WO 00/00479 discloses 1,3-benzodiazapines of the formula:

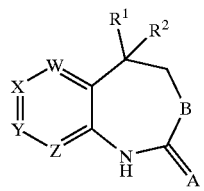

wherein A is O or S. Compounds of this type are not considered part of the present invention.

Even with the current success of reverse transcriptase inhibitors, it has been found that HIV patients can become resistant to a single inhibitor. Thus, it is desirable to develop additional inhibitors to further combat HIV infection.

SUMMARY OF THE INVENTION

Accordingly, one aspect of the present invention is to provide novel reverse transcriptase inhibitors.

The present invention further provides a novel method of treating HIV infection which comprises administering to a host in need of such treatment a therapeutically effective amount of at least one of the compounds of the present invention or a pharmaceutically acceptable salt form thereof.

The present invention provides a novel method of treating HIV infection which comprises administering to a host in need thereof a therapeutically effective combination of (a) one of the compounds of the present invention and (b) one or more compounds selected from the group consisting of HIV reverse transcriptase inhibitors and HIV protease inhibitors.

The present invention provides pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

The present invention provides a method of inhibiting HIV present in a body fluid sample which comprises treating the body fluid sample with an effective amount of a compound of the present invention.

The present invention provides a kit or container containing at least one of the compounds of the present invention in an amount effective for use as a standard or reagent in a test or assay for determining the ability of a potential pharmaceutical to inhibit HIV reverse transcriptase, HIV growth, or both.

The present invention provides novel compounds for use in therapy.

The present invention provides the use of novel compounds for the manufacture of a medicament for the treatment of HIV.

These and other objects, which will become apparent during the following detailed description, have been achieved by the inventors' discovery that compounds of formula (I):

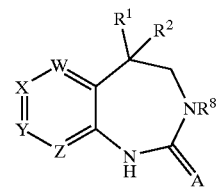

wherein $R^1$, $R^2$, $R^8$, W, X, Y, Z, and A are defined below, stereoisomeric forms, mixtures of stereoisomeric forms, or pharmaceutically acceptable salt forms thereof, are effective reverse transcriptase inhibitors.

DETAILED DESCRIPTION OF PREFERRED EMBODIMENTS

[1] Thus, in an embodiment, the present invention provides a novel compound of formula I:

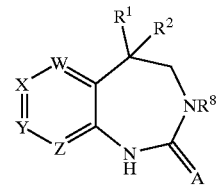

or a stereoisomer or pharmaceutically acceptable salt form thereof, wherein:

A is N—CN, N—CONH$_2$, or N—OR$^{11}$;
W is N or CR$^3$;
X is N or CR$^{3a}$;
Y is N or CR$^{3b}$;
Z is N or CR$^{3c}$;
provided that if two of W, X, Y, and Z are N, then the remaining are other than N;
$R^1$ is selected from the group C$_{1-3}$ alkyl substituted with 0–7 halogen and cyclopropyl;
$R^2$ is selected from the group —R$^{2c}$, —OR$^{2c}$, —OCHR$^{2a}$R$^{2b}$, —OCH$_2$CHR$^{2a}$R$^{2b}$, —O(CH$_2$)$_2$CHR$^{2a}$R$^{2b}$, —OCHR$^{2a}$C=C—R$^{2b}$, —OCHR$^{2a}$C=R$^{2c}$, —OCHR$^{2a}$C≡C—R$^{2b}$, —SR$^{2c}$, —SCHR$^{2a}$R$^{2b}$, —SCH$_2$CHR$^{2a}$R$^{2b}$, —S(CH$_2$)$_2$CHR$^{2a}$R$^{2b}$, —SCHR$^{2a}$C=C—R$^{2b}$, —SCHR$^{2a}$C=R$^{2c}$, —SCHR$^{2a}$C≡C—R$^{2b}$, —NR$^{2a}$R$^{2c}$, —NHCHR$^{2a}$R$^{2b}$, —NHCH$_2$CHR$^{2a}$R$^{2b}$, —NH(CH$_2$)$_2$CHR$^{2a}$R$^{2b}$, —NHCHR$^{2a}$C=C—R$^{2b}$, —NHCHR$^{2a}$C=R$^{2c}$, and —NHCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-6}$ alkyl substituted with 0–2 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, phenyl substituted with 0–2 R$^{3d}$, and 3–6 membered heterocyclic group containing 1–3 heteroatoms selected from the group O, N, and S, substituted with 0–2 R$^{3d}$;

alternatively, the group —NR$^{2a}$R$^{2c}$ represents a 4–7 membered cyclic amine, wherein 0–1 carbon atoms are replaced by O or NR$^5$;

R$^3$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;

R$^{3a}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3a}$ and R$^{3b}$ together form —OCH$_2$O—;

R$^{3c}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3g}$, at each occurrence, is independently selected from the group C$_{1-4}$ alkyl, C$_{2-5}$ alkenyl, —OH, C$_{1-4}$ alkoxy, OCF$_3$, F, Cl, Br, I, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, C$_{3-10}$ carbocycle substituted with 0–3 R$^{3f}$ and a 5–10 membered heterocyclic group containing 1–3 heteroatoms selected from the group O, N, and S, substituted with 0–3 R$^{3f}$; and, R$^4$ is selected from the group F, Cl, Br, I, C$_{1-6}$ alkyl substituted with 0–2 R$^{3e}$, C$_{3-10}$ carbocycle substituted with 0–2 R$^{3e}$, phenyl substituted with 0–5 R$^{3e}$, and a 5–10 membered heterocyclic group containing 1–3 heteroatoms selected from the group O, N, and S, substituted with 0–2 R$^{3e}$;

R$^5$ and R$^{5a}$ at each occurrence are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group C$_{1-3}$ alkyl and C$_{1-3}$ alkoxy;

R$^8$ is selected from the group H, OR$^9$, SR$^9$, NR$^5$R$^9$, C$_{1-6}$ alkyl substituted with 0–3 R$^{3g}$, C$_{2-6}$ alkenyl substituted with 0–3 R$^{3g}$, C$_{2-6}$ alkynyl substituted with 0–3 R$^{3g}$, C$_{3-5}$ cycloalkyl substituted with 0–2 R$^{3f}$, phenyl substituted with 0–5 R$^{3f}$, and a 5–6 membered heterocyclic group containing 1–3 heteroatoms selected from the group O, N, and S, substituted with 0–2 R$^{3f}$;

R$^9$ is selected from the group C$_{3-10}$ carbocycle substituted with 0–5 R$^{3f}$ and a 5–10 membered heterocyclic group containing 1–3 heteroatoms selected from the group O, N, and S, substituted with 0–2 R$^{3f}$;

R$^{10}$ is selected from the group C$_{1-4}$ alkyl and phenyl; and

R$^{11}$ is selected from the group H and C$_{1-4}$ alkyl.

[2] In a preferred embodiment, the present invention provides a novel compound of formula I, wherein:

R$^1$ is selected from the group C$_{1-3}$ alkyl substituted with 1–7 halogen and cyclopropyl;

R$^2$ is selected from the group —R$^{2c}$, —OR$^{2c}$, —OCHR$^{2a}$R$^{2b}$, —OCH$_2$CHR$^{2a}$R$^{2b}$, —O(CH$_2$)$_2$CHR$^{2a}$R$^{2b}$, —OCHR$^{2a}$C=C—R$^{2b}$, —OCHR$^{2a}$C=R$^{2c}$, —OCHR$^{2a}$C≡C—R$^{2b}$, —SR$^{2c}$, —SCHR$^{2a}$R$^{2b}$, —SCH$_2$CHR$^{2a}$R$^{2b}$, —S(CH$_2$)$_2$CHR$^{2a}$R$^{2b}$, —SCHR$^{2a}$C=C—R$^{2b}$, —SCHR$^{2a}$C=R$^{2c}$, and —SCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group C$_{1-5}$ alkyl substituted with 0–2 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, and phenyl substituted with 0–2 R$^{3d}$;

R$^3$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

R$^{3a}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^{3a}$ and R$^{3b}$ together form —OCH$_2$O—;

R$^4$ is selected from the group Cl, F, C$_{1-4}$ alkyl substituted with 0–2 R$^{3e}$, C$_{3-5}$ carbocycle substituted with 0–2 R$^{3e}$, phenyl substituted with 0–5 R$^{3e}$, and a 5–6 membered heterocyclic group containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$;

R$^7$ is selected from the group CH$_3$, C$_2$H$_5$, CH(CH$_3$)$_2$, OCH$_3$, OC$_2$H$_5$, and OCH(CH$_3$)$_2$; and, $R^8$ is selected from the group H, cyclopropyl, $CH_3$, $C_2H_5$, and $CH(CH_3)_2$.

[3] In a more preferred embodiment, the present invention provides a novel compound of formula I, wherein:
$R^1$ is selected from the group $CF_3$, $C_2F_5$, and cyclopropyl;
$R^2$ is selected from the group —$R^{2c}$, —$OR^{2c}$, —$OCHR^{2a}R^{2b}$, —$OCH_2CHR^{2a}R^{2b}$, —$OCHR^{2a}C$=C—$R^{2b}$, —$OCHR^{2a}C$=$R^{2c}$, —$OCHR^{2a}C$≡C—$R^{2b}$, —$SR^{2c}$, —$SCHR^{2a}R^{2b}$, —$SCH_2CHR^{2a}R^{2b}$, —$SCHR^{2a}C$=C—$R^{2b}$, —$SCHR^{2a}C$=$R^{2c}$, and —$SCHR^{2a}C$≡C—$R^{2b}$;
$R^{2a}$ is selected from the group H, $CH_3$, $CH_2CH_3$, $CH(CH_3)_2$, and $CH_2CH_2CH_3$;
$R^{2b}$ is H or $R^{2c}$;
$R^{2c}$ is selected from the group $C_{1-3}$ alkyl substituted with 0–2 $R^4$, $C_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$;
$R^3$, at each occurrence, is independently selected from the group H, $C_{1-3}$ alkyl, OH, $C_{1-3}$ alkoxy, F, Cl, Br, I, $NR^5R^{5a}$, $NO_2$, —CN, $C(O)R^6$, $NHC(O)R^7$, and $NHC(O)NR^5R^{5a}$;
alternatively, $R^3$ and $R^{3a}$ together form —$OCH_2O$—;
$R^{3b}$ is H;
$R^{3c}$ is H;
$R^{3e}$, at each occurrence, is independently selected from the group H, $C_{1-4}$ alkyl, —OH, $C_{1-4}$ alkoxy, $OCF_3$, F, Cl, —$NR^5R^{5a}$, —$C(O)R^6$, and —$SO_2NR^5R^{5a}$;
$R^4$ is selected from the group Cl, F, $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic group containing 1–3 heteroatoms selected from the group O, N, and S, substituted with 0–1 $R^{3e}$;
$R^5$ and $R^{5a}$ are independently selected from the group H, $CH_3$ and $C_2H_5$;
$R^6$ is selected from the group H, OH, $CH_3$, $C_2H_5$, $OCH_3$, $OC_2H_5$, and $NR^5R^{5a}$;
$R^7$ is selected from the group $CH_3$, $C_2H_5$, $OCH_3$, and $OC_2H_5$; and,
$R^8$ is selected from the group H, cyclopropyl, $CH_3$, and $C_2H_5$.

[4] In an even more preferred embodiment, the present invention provides a novel compound of formula I, wherein:
$R^1$ is $CF_3$;
$R^2$ is selected from the group —$R^{2c}$, —$OR^{2c}$, —$OCH_2R^{2b}$, —$OCH_2CH_2R^{2b}$, —$OCH_2C$=C—$R^{2b}$, —$OCH_2C$≡C—$R^{2b}$, —$SR^{2c}$, —$SCH_2R^{2b}$, —$SCH_2CH_2R^{2b}$, —$SCH_2C$=C—$R^{2b}$, and —$SCH_2C$≡C—$R^{2b}$;
$R^{2b}$ is H or $R^{2c}$;
$R^{2c}$ is selected from the group methyl substituted with 0–2 $R^4$, ethyl substituted with 0–2 $R^4$, propyl substituted with 0–2 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$;
$R^3$, at each occurrence, is independently selected from the group H, $C_{1-3}$ alkyl, OH, $C_{1-3}$ alkoxy, F, Cl, $NR^5R^{5a}$, $NO_2$, —CN, and $C(O)R^6$;
alternatively, $R^3$ and $R^{3a}$ together form —$OCH_2O$—;
$R^{3d}$, at each occurrence, is independently selected from the group $CH_3$, —OH, $OCH_3$, $OCF_3$, F, Cl, and —$NR^5R^{5a}$;
$R^{3e}$, at each occurrence, is independently selected from the group $CH_3$, —OH, $OCH_3$, $OCF_3$, F, Cl, and —$NR^5R^{5a}$;
$R^4$ is selected from the group Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic group containing 1–3 heteroatoms selected from the group O, N, and S, substituted with 0–1 $R^{3e}$, wherein the heterocyclic group is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;
$R^5$ and $R^{5a}$ are independently selected from the group H, $CH_3$ and $C_2H_5$;
$R^6$ is selected from the group H, OH, $CH_3$, $C_2H_5$, $OCH_3$, $OC_2H_5$, and $NR^5R^{5a}$;
$R^7$ is selected from the group $CH_3$, $C_2H_5$, $OCH_3$, and $OC_2H_5$; and,
$R^8$ is selected from the group H, cyclopropyl, and $C_2H_5$.

[5] In a further preferred embodiment, wherein the compound is of formula Ia

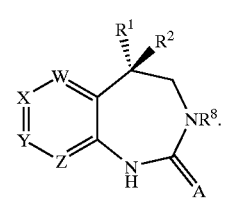

Ia

[6] In a further preferred embodiment, wherein the compound is of formula Ib:

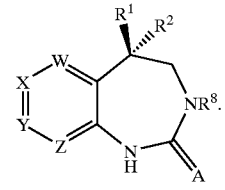

Ib

[7] In a further preferred embodiment, the compound of formula I is selected from the group:
7-chloro-2-cyanoimino-5-(cyclopropylmethyloxy)-1,5-dihydro-5-trifluoromethyl-1,3-benzodiazepine;
7-chloro-2-cyanoimino-5-(cyclobutylmethyloxy)-1,5-dihydro-5-trifluoromethyl-1,3-benzodiazepine;
7-chloro-2-cyanoimino-5-(cyclopropylmethyloxy)-1,5-dihydro-3-ethyl-5-trifluoromethyl-1,3-benzodiazepine;
7-chloro-5-cyclopropylmethyloxy-1,5-dihydro-2-methoxyimino-5-trifluoromethyl-1,3-benzodiazepine;
7-chloro-5-cyclopropylmethyloxy-1,5-dihydro-3-ethyl-2-methoxyimino-5-trifluoromethyl-1,3-benzodiazepine;
or a pharmaceutically acceptable salt form thereof.

[8] In another further preferred embodiment, the compound of formula I is selected from the group:
(S)-7-chloro-2-cyanoimino-5-(cyclopropylmethyloxy)-1,5-dihydro-5-trifluoromethyl-1,3-benzodiazepine;
(S)-7-chloro-2-cyanoimino-5-(cyclobutylmethyloxy)-1,5-dihydro-5-trifluoromethyl-1,3-benzodiazepine;
(S)-7-chloro-2-cyanoimino-5-(cyclopropylmethyloxy)-1,5-dihydro-3-ethyl-5-trifluoromethyl-1,3-benzodiazepine;
(S)-7-chloro-5-cyclopropylmethyloxy-1,5-dihydro-2-methoxyimino-5-trifluoromethyl-1,3-benzodiazepine;

(S)-7-chloro-5-cyclopropylmethyloxy-1,5-dihydro-3-ethyl-2-methoxyimino-5-trifluoromethyl-1,3-benzodiazepine;
or a pharmaceutically acceptable salt form thereof.

[9] In another further preferred embodiment, the compound of formula I is selected from the group:
(R)-7-chloro-2-cyanoimino-5-(cyclopropylmethyloxy)-1,5-dihydro-5-trifluoromethyl-1,3-benzodiazepine;
(R)-7-chloro-2-cyanoimino-5-(cyclobutylmethyloxy)-1,5-dihydro-5-trifluoromethyl-1,3-benzodiazepine;
(R)-7-chloro-2-cyanoimino-5-(cyclopropylmethyloxy)-1,5-dihydro-3-ethyl-5-trifluoromethyl-1,3-benzodiazepine;
(R)-7-chloro-5-cyclopropylmethyloxy-1,5-dihydro-2-methoxyimino-5-trifluoromethyl-1,3-benzodiazepine;
(R)-7-chloro-5-cyclopropylmethyloxy-1,5-dihydro-3-ethyl-2-methoxyimino-5-trifluoromethyl-1,3-benzodiazepine;
or a pharmaceutically acceptable salt form thereof.

In another embodiment, the present invention provides compounds of formula I wherein $R^1$ is $CF_3$.

In another embodiment, the present invention provides compounds of formula I wherein $R^2$ is $OR^{2c}$; $R^{2c}$ is methyl substituted with 0–2 $R^4$; and $R^4$ is selected from cyclopropyl and cyclobutyl.

In another embodiment, the present invention provides compounds of formula I wherein A is C—CN.

In another embodiment, the present invention provides compounds of formula I wherein A is N—$CONH_2$.

In another embodiment, the present invention provides compounds of formula I wherein A is N—$OR^{11}$; and $R^{11}$ is selected from H, methyl, ethyl, propyl, i-propyl and butyl.

In another embodiment, the present invention provides compounds of formula I wherein W is $CR^3$; X is $CR^{3a}$; Y is $CR^{3b}$; and Z is $CR^{3c}$.

In another embodiment, the present invention provides compounds of formula I wherein $R^3$, $R^{3b}$, and $R^{3c}$ are H; and $R^{3a}$ is selected from H, Cl, F, and Br.

In another embodiment, the present invention provides compounds of formula I wherein $R^8$ is selected from H, methyl, ethyl, and propyl.

In another embodiment, the present invention provides compounds of formula I wherein $R^8$ is H.

In another embodiment, the present invention provides a novel pharmaceutical composition comprising a pharmaceutically acceptable carrier and a therapeutically effective amount of a compound of formula I or pharmaceutically acceptable salt form thereof.

In another embodiment, the present invention provides a novel method of treating HIV infection which comprises administering to a host in need of such treatment a therapeutically effective amount of a compound of formula I or pharmaceutically acceptable salt form thereof.

In another embodiment, the present invention provides a novel method of treating HIV infection which comprises administering, in combination, to a host in need thereof a therapeutically effective amount of:
(a) a compound of formula I; and,
(b) at least one compound selected from the group consisting of HIV reverse transcriptase inhibitors and HIV protease inhibitors.

In another preferred embodiment, the reverse transcriptase inhibitor is selected from the group AZT, ddC, ddI, d4T, 3TC, DPC082, DPC083, DPC961, DPC963, AG1549 delavirdine, efavirenz, nevirapine, Ro 18,893, trovirdine, MKC-442, HBY 097, ACT, UC-781, UC-782, RD4-2025, and MEN 10979, and the protease inhibitor is selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In an even more preferred embodiment, the reverse transcriptase inhibitor is selected from the group AZT, efavirenz, and 3TC and the protease inhibitor is selected from the group saquinavir, ritonavir, nelfinavir, and indinavir.

In a still further preferred embodiment, the reverse transcriptase inhibitor is AZT.

In another still further preferred embodiment, the protease inhibitor is indinavir.

In another embodiment, the present invention provides a pharmaceutical kit useful for the treatment of HIV infection, which comprises a therapeutically effective amount of:
(a) a compound of formula I or a pharmaceutically acceptable salt form thereof; and,
(b) at least one compound selected from the group consisting of HIV reverse transcriptase inhibitors and HIV protease inhibitors, in one or more sterile containers.

In another embodiment, the present invention provides novel compounds of formula I or pharmaceutically acceptable salt forms thereof for use in therapy.

In another embodiment, the present invention provides the use of novel compounds of formula I or pharmaceutically acceptable salt forms thereof for the manufacture of a medicament for the treatment of HIV.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-6}$ alkyl (or alkylene), is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-10}$ cycloalkyl, is intended to include $C_3$, $C_4$, $C_5$, $C_6$, $C_7$, $C_8$, $C_9$, and $C_{10}$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-6}$ alkenyl (or alkenylene), is intended to include $C_2$, $C_3$, $C_4$, $C_5$, and $C_6$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-6}$ alkynyl (or alkynylene), is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic group" is intended to mean any stable 3, 4, 5, 6, or 7-membered monocyclic or bicyclic or 7, 8, 9, or 10-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benztriazolyl, benzisoxazolyl, oxindolyl, benzoxazolinyl, and isatinoyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Also included is Glaxo's combination of AZT and 3TC. Examples of non-nucleoside RT inhibitors include, but are no limited to, DPC082 (Bristol-Myers Squibb), (+)-4-Cyclopropylethenyl-5,6-difluoro-4-trifluoromethyl-3,4-dihydro-2(1H)-quinazolinone), DPC083 (Bristol-Myers Squibb), (−)-6-chloro-4-E-cyclopropylethenyl-4-trifluoromethyl-3,4-dihydro-2(1H)-quinazolinone), $DPC_{961}$ (Bristol-Myers Squibb), (−)-6-chloro-4-cyclopropylethynyl-4-trifluoromethyl-3,4-dihydro-2(1H)-quinazolinone), $DPC_{963}$ (Bristol-Myers Squibb), (+)-4-Cyclopropylethynyl-5,6-difluoro-4-trifluoromethyl-3,4-dihydro-2(1H)-quinazolinone), AG1549 (Warner Lambert/Shionogi), delavirdine (Pharmacia and Upjohn U90152S), efavirenz (Bristol-Myers Squibb), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4–2025 (Tosoh Co. Ltd.), and MEN 10979 (Menarini Farmaceutici).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), VX-478 (Vertex/Glaxo Wellcome), nelfinavir (Agouron, AG-1343), KNI-272 (Japan Energy), CGP-61755 (Ciba-Geigy), U-140690 (Pharmacia and Upjohn), and ABT-378. Additional examples include the cyclic protease inhibitors disclosed in WO93/07128, WO 94/19329, WO 94/22840, and PCT Application Number U.S. Pat. Ser. No. 96/03426.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and acetamide, formamide, and benzamide derivatives of amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are contempleted by the present invention.

"Therapeutically effective amount" is intended to include an amount of a compound of the present invention alone or in combination with other active ingredients or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. In the Schemes which follow, $R^1$ is shown as a $CF_3$ group, but could be any one of the presently described $R^1$ groups.

A method for preparing compounds of the present invention, N-cyanoguanadines or N-amidoguanadines, is shown in Scheme 1. A trifluoromethyl ketone 1 is treated with dimethylsulfoxonium methylide, dimethylsulfonium methylide, or diazomethane to give an epoxide 2 which is then reacted with ammonia or a primary amine to give a ring-opened tertiary alcohol 3. For the synthesis of the compounds of this invention where $R^8$=H, the diamino alcohol 3 is cyclized to a cyanoguanadine 4 using diphenyl cyanocarbonimidate or dimethyl cyanodithioimidocarbonate typically in refluxing alcohol. Finally, the alcohol functionality of 4 is reacted with a base, for example, sodium hydride, and an alkyl halide to give compound 6. For the synthesis of the compounds of the invention where $R^8$= alkyl, the diamino alcohol 3 is first reacted with an alkyl halide and base to give a diaminoether 5. The diaminoether 5 is then cyclized using diphenyl cyanocarbonimidate or dimethyl cyanodithioimidocarbonate as before to give compound 6. The cyano functionality in turn can be hydrolyzed to the corresponding amide using, for example, aqueous acid or base to afford compound 7. For an example of an acid catalyzed hydrolysis, see [Adams, P.; et al.; J. Org. Chem., 1952, 17, 1162].

Another method for preparing the diaminoether as well as a method for its conversion to N-alkoxy and N-hydroxyguanadines is shown in Scheme 2. The trityl-protected trifluoromethyl ketone 8 is treated with dimethylsulfoxonium methylide, dimethylsulfonium methylide, or diazomethane to form an epoxide 9. The epoxide 9 is then reacted with sodium azide in tetrahydrofuran to form a ring-opened tertiary alcohol 11. With an alkylating agent alkyl halide and a base the alcohol 11 is first converted to an ether, which is followed by removal of the trityl group under acidic condition and then reduction of the azide functionality to a diaminoether 5 using, for example, lithium aluminum hydride.

SCHEME 1

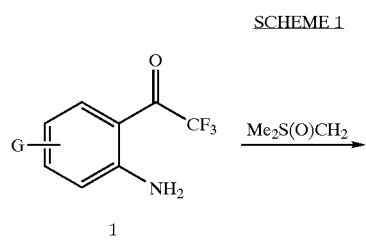

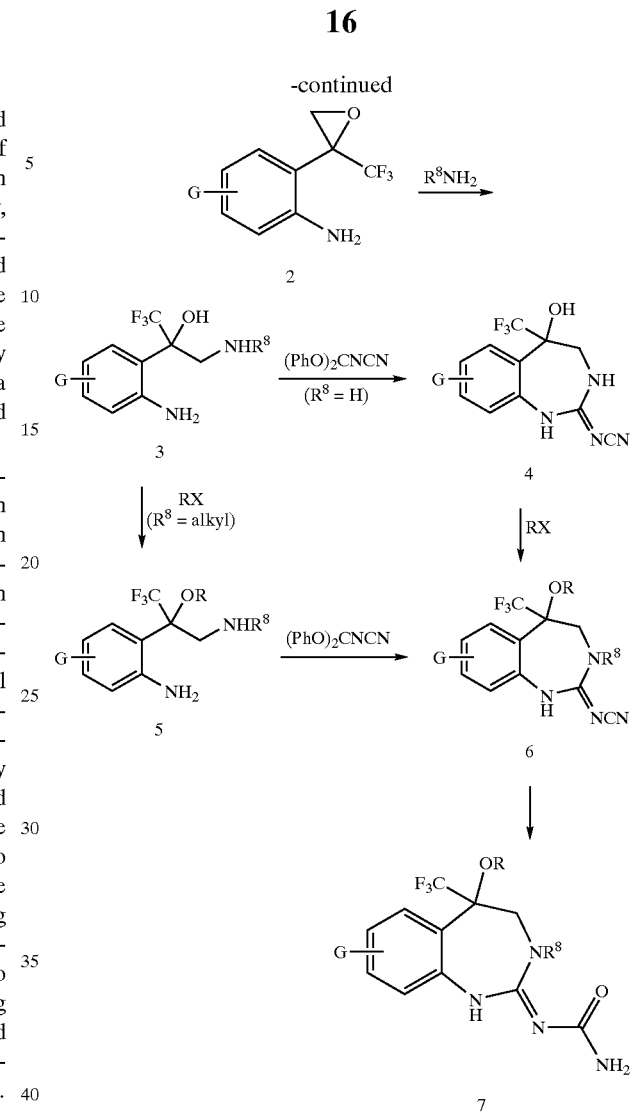

SCHEME 2

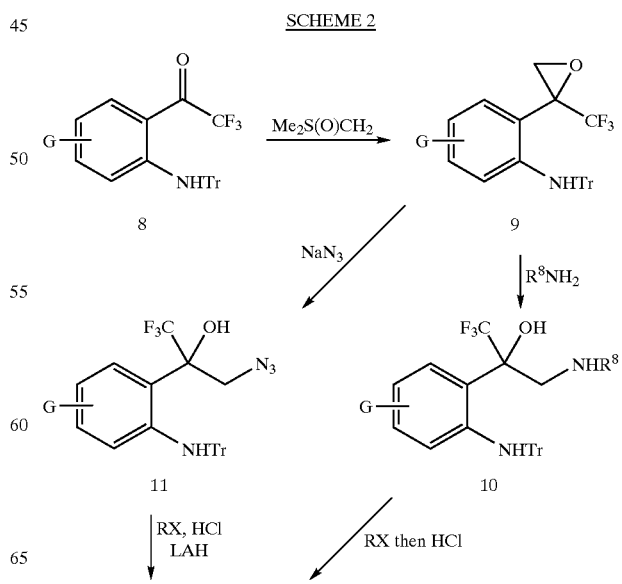

-continued

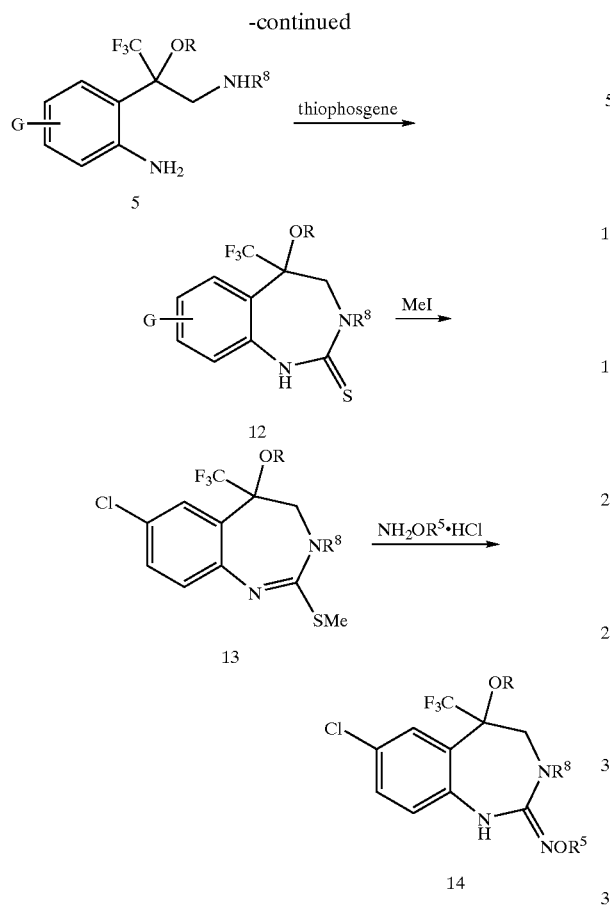

This diaminoether 5 is cyclized with thiophosgene or thiocarbonyldiimdazole to form the cyclic thiourea 12. The thiourea is converted to the corresponding methylthioether 13 with base and iodomethane. Reaction of the thioether with hydroxylamine hydrochloride or an alkoxylamine hydrochloride produces the corresponding N-alkoxy or N-hydroxyguanidine 14. In the case where $R^8$= alkyl, the epoxide 9 is opened with an alkyl amine and the resultant diamine 10 is carried through the same synthetic sequence.

Alternatively, compounds of the present invention may be prepared as shown in Scheme 3. The trityl-protected amino trifluoromethyl ketone is reacted with nitromethane to form an alkoxide. The alkoxide is quenched with a protecting group like TBS-Cl to provide the corresponding silyl ether. This is converted to the nitro-olefin by heating it in the presence of a base (e.g., $K_2CO_3$). $R^2$ (e.g., butyl) can be attached via grignard addition (e.g., BuMgCl), $(R^2)_3Al$ addition (e.g., (cyclopropylethyl)$_3$Al) or other known methods of addition to nitro-olefins. Reduction of the nitro group to an amine followed by deprotection of the aniline amine produces the diaminoether which can be transformed to the corresponding N-cyanoguanidine, N-amidoguanadine, or N-methoxy or N-hydroxyguanadine using techniques depicted in Schemes 1 and 2.

SCHEME 4

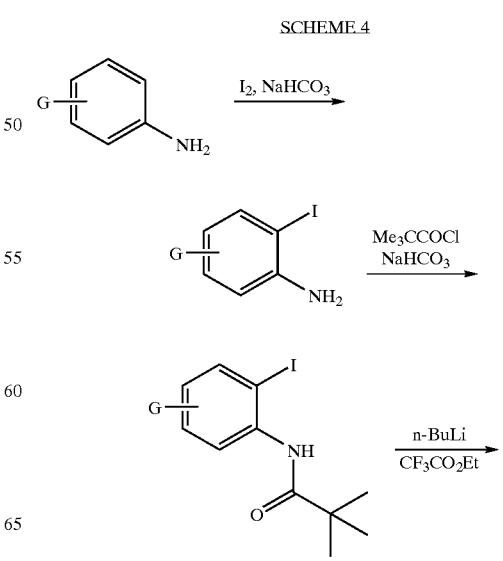

SCHEME 3

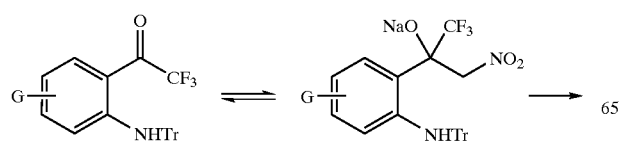

-continued

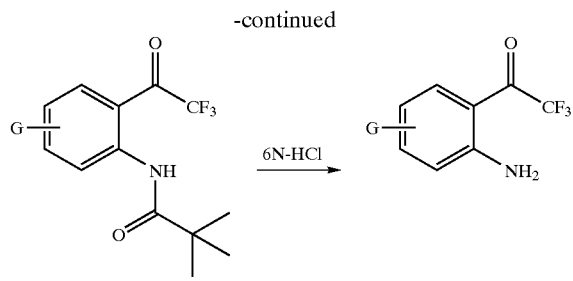

Scheme 4 describes a means of obtaining an amino-ketone useful in the previous schemes. After iodination of an appropriate aniline, the trifluoromethyl group can be introduced using a strong base and ethyl trifluoroacetate.

In addition to the methods of obtaining keto-anilines described previously, nucleophilic opening of isatoic anhydrides can also be used as shown in Scheme 6. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41(6), 825–831; Takimoto et al, *Fukuoka Univ. Sci. Reports* 1985, 15(1), 37–38; Kadin et al, *Synthesis* 1977, 500–501; Staiger et al, *J. Org. Chem.* 1959, 24, 1214–1219.

One enantiomer of a compound of Formula I may display superior activity compared with the other. Thus, the following stereochemistries are considered to be a part of the present invention.

SCHEME 5

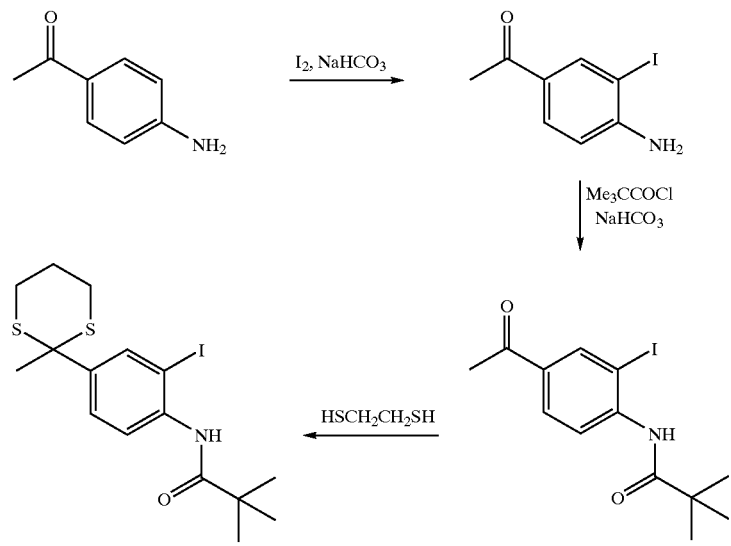

Because certain benzo-substituents are incompatible with the methods of the previous schemes, it may be necessary to protect these groups before forming the desired product. In Scheme 5 there is shown a means of obtaining carbonyl-substituted iodo-anilines which can be modified as shown in Scheme 4. After iodination of an acetyl-aniline, the acetyl group is protected by means well known to those of skill in the art, such as using 1,3-propanedithiol. Deprotection of the ketone can then be achieved using $HgCl_2$ and $HgO$ or other means well known to those of skill in the art.

SCHEME 6

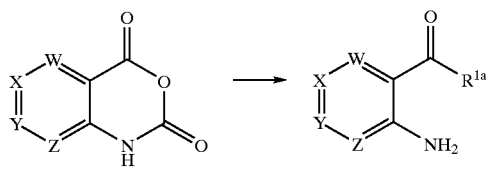

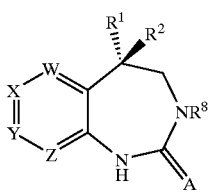

Ia

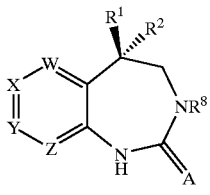

Ib

When required, separation of the racemic material can be achieved by HPLC using a chiral column or by a resolution using a resolving agent such as camphonic chloride as in Thomas J. Tucker, et al, *J. Med. Chem.* 1994, 37, 2437–2444. A chiral compound of Formula I may also be directly synthesized using a chiral catalyst or a chiral ligand, e.g. Mark A. Huffman, et al, *J. Org. Chem.* 1995, 60, 1590–1594.

Other features of the invention will become apparent in the course of the following descriptions of exemplary embodiments which are given for illustration of the invention and are not intended to be limiting thereof.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "ACN" for acetic anhydride, "CDI" for carbonyl diimidazole, "DIEA" for diisopropylethylamine, "DIPEA" for diisopropylethylamine, "DMAP" for dimethylaminopyridine, "DME" for dimethoxyethane, "EDAC" for 1-(3-dimethylaminopropyl)- 3-ethylcarbodiimide hydrochloride, "LAH" for lithium aluminium hydride, "TBAF" for tetrabutylammonium fluoride, "TBS-Cl" for t-butyldimethylsilyl chloride, and "TEA" for triethylamine.

Example 1

Preparation of Compound 6b: 7-chloro-2-cyanoimino-5-(cyclopropylmethyloxy)-1,5-dihydro-5-trifluoromethyl-1,3-benzodiazepine To a solution of dimethylsulfoxonium iodide (7.9 g, 35.8 mmol) in dry DMSO (60 mL) at room temperature was added 95% NaH portion-wise (900 mg, 35.8 mmol). This solution was then added to a solution of amino ketone 1a in 90 mL of dry THF. The reaction mixture was treated immediately with water and was then extracted with EtOAc. The organic phase was dried over MgSO$_4$, filtered and concentrated in vacuo to provide epoxide 2a in quantitative yield. Epoxide 2a was used without further purification in the next step of the synthetic sequence.

The epoxide 2a was dissolved in EtOH (50 mL) and was treated with excess 2M ammonia in EtOH. The resulting solution was heated to 45° C. for 2 days. The volatiles were removed in vacuo and the remaining oil was purified using column chromatography (50% EtOAc/hexanes). The diamino alcohol 3a was isolated as a yellow oil (3.3 g, 73%) and was used without further purification.

A solution 3a (100 mg, 0.39 mmol) and diphenyl cyanocarbonimidate (93 mg, 0.39 mmol) in iPrOH (5 mL) was refluxed for 12 h. The solvent was removed in vacuo. Upon addition of dichloromethane to the remaining oily residue, a precipitate formed. This was collected by filtration to provide 90 mg (75%) of alcohol 6a that was used directly in the next step of the synthesis.

To a solution of alcohol 6a (250 mg, 0.82 mmol) in dry DMSO (4 mL) was added 95% NaH (41.0 mg, 1.64 mmol). After 15 minutes, (bromomethyl)cyclopropane (0.480 mL, 4.92 mmol) was added. After 15 minutes, another 0.240 mL (2.46 mmol) of (bromomethyl)cyclopropane was added. After another 15 minutes, the reaction mixture was poured into saturated NH$_4$Cl and was extracted 3 times with EtOAc. The combined organic phases were dried over MgSO$_4$, filtered and concentrated. The crude product was purified using column chromatography (40% EtOAc/hexanes) to

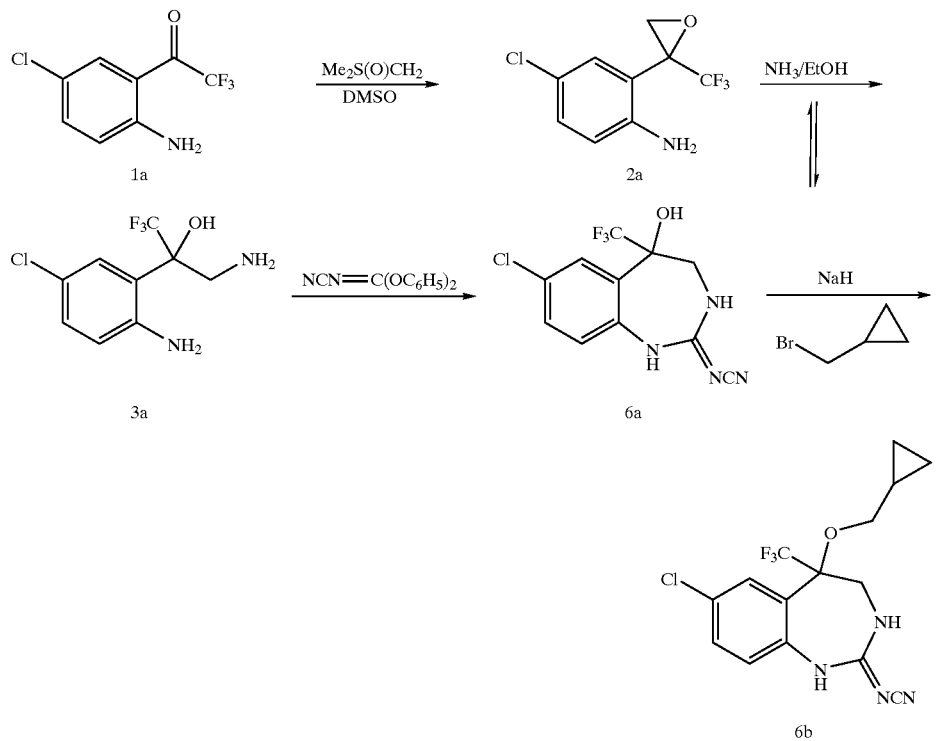

provide the crude cyanoguanadine 6b, which was recrystallized from 2% MeOH/CH$_2$Cl$_2$, yielding 35 mg (11%, mp 291–293° C.) of pure 6b.

Example 2

Preparation of Compound 6c: 7-chloro-2-cyanoimino-5-(cyclobutylmethyloxy)-1,5-dihydro-5-trifluoromethyl-1,3-benzodiazepine

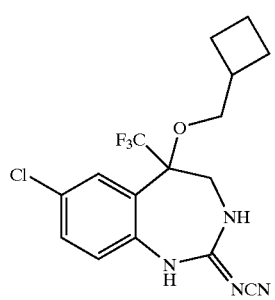

6c

To a solution of alcohol 6a (200 mg, 0.66 mmol) in dry DMSO (4 mL) was added 95% NaH (28 mg, 1.12 mmol). After gas evolution had ceased, (bromomethyl)cyclobutane (0.445 mL, 3.96 mmol) was added. After another 15 minutes, the same amounts of both NaH and (bromomethyl)cyclobutane were added again. This addition was repeated two more times before the reaction mixture was quenched with saturated NH$_4$Cl. The aqueous phase was extracted one time with EtOAc. The organic phase was dried over MgSO$_4$, filtered and concentrated, and then the crude product was purified via column chromatography (20% EtOAc/CH$_2$Cl$_2$) to provide 55 mg (22%) of the title compound 6c in the form of a white solid (mp 239–241° C.).

Example 3

Preparation of Compound 6d: 7-chloro-2-cyanoimino-5-(cyclopropylmethyloxy)-1,5-dihydro-3-ethyl-5-trifluoromethyl-1,3-benzodiazepine

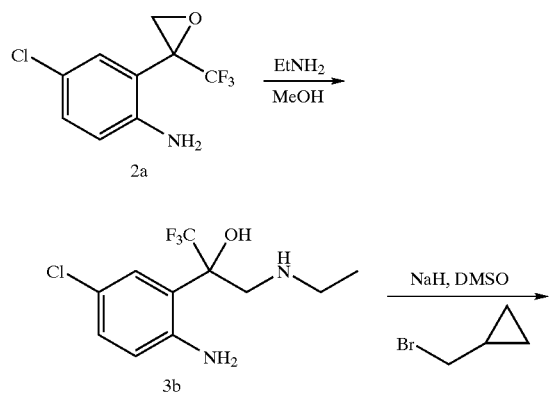

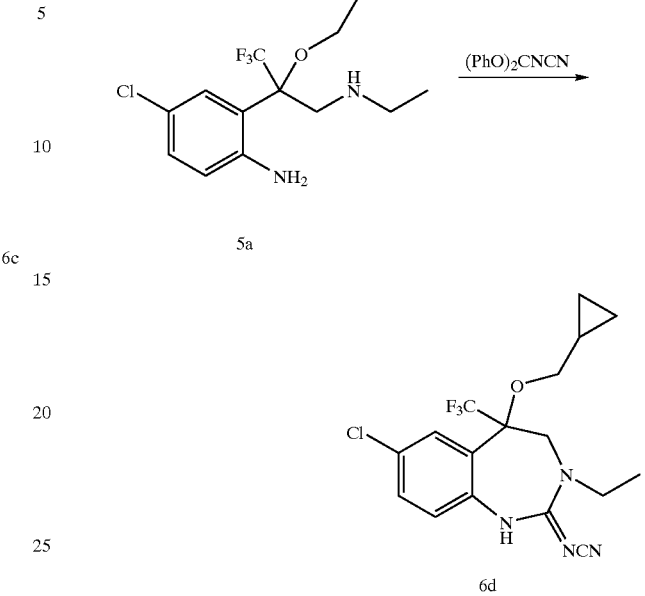

To the epoxide 2a (5.3 g, 22.4 mmol) was added 23 mL of 2M ethylamine in MeOH. The reaction mixture was stirred at room temperature for 12 h and was then heated to 60° C. for 1 h. The solvent was removed in vacuo and the crude product was purified using column chromatography (20% EtOAc/hexanes), providing 4.8 g (76%) of the alcohol 3b, which was isolated as a thick yellow oil.

To a solution of alcohol 3b (589 mg, 2.1 mmol) in dry DMSO (15 mL) at room temperature was added 95% NaH (68 mg, 2.7 mmol). After 10 min, (bromomethyl)cyclopropane (0.600 mL, 6.2 mmol) was added. The reaction mixture was stirred for 45 min upon which time it was poured into saturated NH$_4$Cl and was extracted with EtOAc. The organic phase was dried over MgSO$_4$, filtered and concentrated. The crude product was purified via column chromatography (40% EtOAc/hexanes) to provide 340 mg (48%) of diamine 5a in the form of a yellow oil.

A solution of diamine 5a (100 mg, 0.30 mmol) and diphenyl cyanocarbonimidate (71 mg, 0.30 mmol) in iPrOH (6 mL) was refluxed overnight. The solvent was removed in vacuo and the crude product was purified via column chromatography (5% Et$_2$O/CH$_2$Cl$_2$) to provide 25 mg (22%, mp 200–203° C.) of the title compound 6d.

Example 4

Preparation of Compound 12: 7-chloro-5-cyclopropylmethyloxy-1,5-dihydro-2-methoxyimino-5-trifluoromethyl-1,3-benzodiazepine The trityl-protected epoxide 9b was prepared according to the method described in Example 1 for the preparation of epoxide 2a using the corresponding tritylated ketone. To a suspension of 9b (7.5 g, 15.6 mmol) in dry DMSO (78 mL) was added NaN$_3$ (1.2 g, 18.7 mmol). The reaction mixture was stirred at room temperature for 2 h, was diluted with EtOAc, and was then poured into brine. The organic phase was seperated and was washed with water and then again with brine. The organic phase was dried over MgSO$_4$, filtered and concentrated. Trituration with heptane for 12 h provided 5.5 g (67%) of pure alcohol 11a in the form of a white powder.

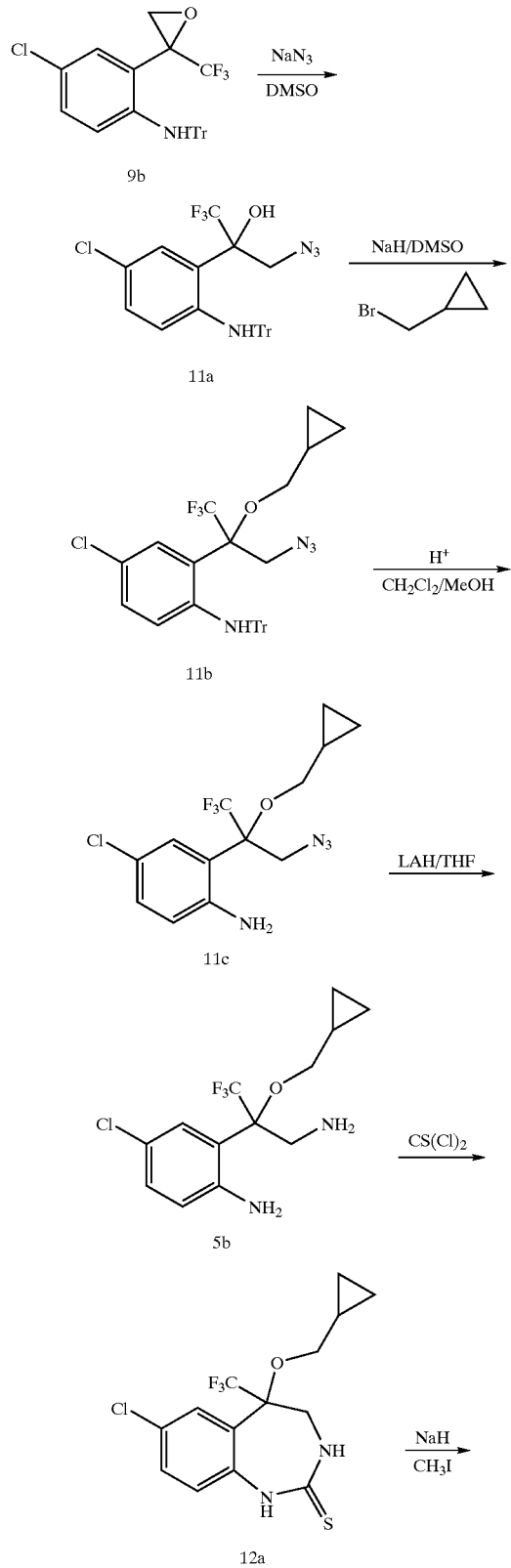

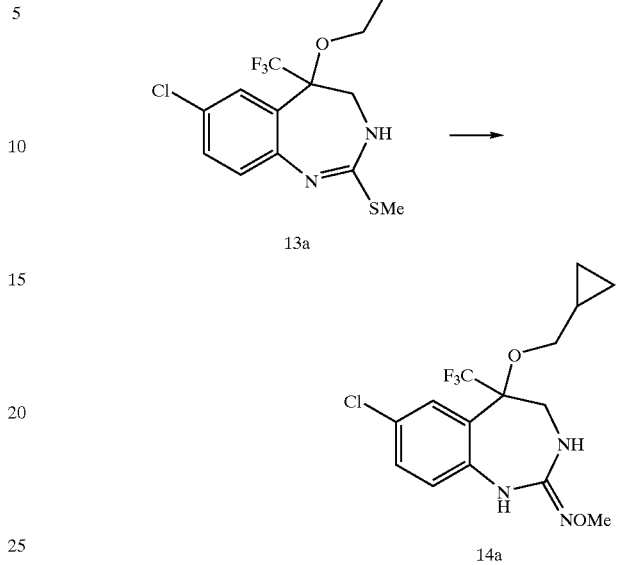

Alcohol 11a (5.5 g, 10.5 mmol) in dry DMSO (50 mL) at room temperature was treated with 95% NaH (530 mg, 21.0 mmol) and then with (bromomethyl)cyclopropane (5.1 mL, 52.5 mmol). After stirring for 30 min, the reaction mixture was poured into saturated $NH_4Cl$ and was extracted once with EtOAc. The organic phase was washed with brine and was then dried over $MgSO_4$, filtered and concentrated. The product was isolated using column chromatography (10% EtOAc/hexanes), providing 2.64 g (44%) of pure 11b.

Trityl-protected azide 11b (2.64 g, 4.5 mmol) was dissolved in 1:1 $CH_2Cl_2$:MeOH (40 mL). To this solution was added 1.32 mL of 6N HCl. After stirring at room temperature for 2 h, the solvent was removed in vacuo. The remaining residue was washed with heptane and was then diluted with EtOAc and extracted once with saturated $NaHCO_3$. The organic phase was dried over $MgSO_4$, filtered and concentrated to provide in quantitative yield the desired azido compound 11c that was used in the next step of the synthesis without further purification.

To a solution of azide 11c (536 mg, 1.6 mmol) in dry THF (8 mL) at 0° C. was added LAH (1M in THF, 1.76 mmol) dropwise. After 2 h, the reaction was poured into 1N NaOH and was extracted with EtOAc. The organic phase was dried over $MgSO_4$, filtered, concentrated, and purified via column chromatography (70% EtOAc/hexanes) to provide 176 mg (36%) of the pure diamine 5b.

A solution of 5b (176 mg, 0.57 mmol) in 3 mL of dry toluene was treated with diisopropylethylamine (0.35 mL, 2.0 mmol) followed by thiophosgene (0.06 mL, 0.74 mmol). After stirring for 1.5 h at room temperature, the reaction mixture was poured into water and was extracted with EtOAc. The organic phase was dried over $MgSO_4$, filtered, and concentrated, then purified using column chromatography (30% EtOAc/hexanes) to provide 74 mg (37%) of the desired thiourea 12a.

To a solution of 12a (37 mg, 0.10 mmol) in dry DMF (0.5 mL) at room temperature was added 95% NaH (3 mg, 0.11 mmol). After gas evolution was complete, iodomethane (0.12 mL, 0.2 mmol) was added. The reaction mixture was stirred for 2 h and was then diluted with EtOAc and was extracted with water. The organic phase was dried over MgSO₄, filtered, concentrated, and then purified via column chromatography (10% EtOAc/hexanes) to provide 37 mg (100%) of the desired thioether 13a.

A mixture of 13a (37 mg, 0.10 mmol), methoxylamine hydrochloride (10 mg, 0.12 mmol) and 1 mL of pyridine was refluxed for 1.5 h. After the mixture had cooled it was poured into water and was extracted with EtOAc. The organic phase was dried over MgSO₄, filtered, concentrated and purified using column chromatography (40% EtOAc/hexanes) to provide 20 mg of 14a on the form of a yellow oil. $^1$H NMR (300 MHz, acetone-d6) δ 7.50 (d, 1H, J=1.2 Hz), 7.25 (dd, 1H, J=8.7, 2.4 Hz), 7.15 (d, 1H, J=8.7 Hz), 8.89–3.78 (m, 1H), 3.50 (dd, 1 H, J=9.6, 6.6 Hz), 3.41 (s, 3H), 2.95 (dd, 1H, J=9.6, 7.5 Hz), 2.71 (d, 1H, J=9.9 Hz), 1.02–0.86 (m, 1H), 0.48–0.34 (m, 2H), 0.17–0.00 (m, 2H).

Example 5

Preparation of Compound 14b: 7-chloro-5-cyclopropylmethyloxy-1,5-dihydro-3-ethyl-2-methoxyimino-5-trifluoromethyl-1,3- benzodiazepine

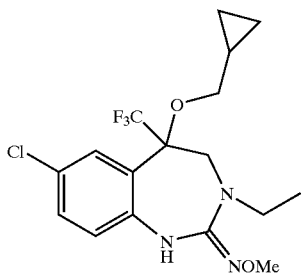

14b

The title compound was prepared as described in Example 4 using diamine 5a as the starting material, beginning with step 5 of the synthetic sequence. $^1$H NMR (300 MHz, CDCl₃) δ 7.64 (s, 1H), 7.28–7.21 (m, 1H), 6.82 (d, 1H, J=9.0 Hz), 3.74 (s, 3H)m 3.78–3.62 (m, 2H), 3.46–3.31 (m, 2H), 3.28–3.12 (m, 1H), 3.04 (dd, 1H. J= 7.2, 2.4 Hz), 1.19 (t, 3H, J=7.2 Hz), 1.16–0.87 (m, 1 H), 0.61–0.50 (m, 2H), 0.21–0.03 (m, 2H).

TABLE 1*

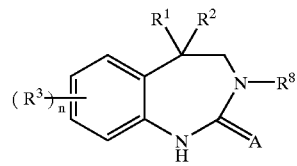

| Ex. # | Cp | R³ | R¹ | R² | A | R⁸ | m.p. (° C.) |
|---|---|---|---|---|---|---|---|
| 1 | 6b | 7-Cl | CF₃ | O—CH₂-cycPr | NCN | H | 291–293 |
| 2 | 6c | 7-Cl | CF₃ | O—CH₂-cycBu | NCN | H | 239–241 |
| 3 | 6d | 7-Cl | CF₃ | O—CH₂-cycPr | NCN | Et | 200–203 |
| 4 | 14a | 7-Cl | CF₃ | O—CH₂-cycPr | NOMe | H | — |
| 5 | 14b | 7-Cl | CF₃ | O—CH₂-cycPr | NOMe | Et | — |

*Unless otherwise indicated, stereochemisty at each asymmetric center can be either R or S, or both cis and trans geometric isomers of a structure are intended unless a specific geometric isomer is indicated.

The following table contains representative examples of the present invention. Each entry in the table is intended to be paired with each formulae at the start of the table. For example, entry 1 in Table 2 is intended to be paired with a-nn and a'-nn'.

TABLE 2*

TABLE 2*-continued
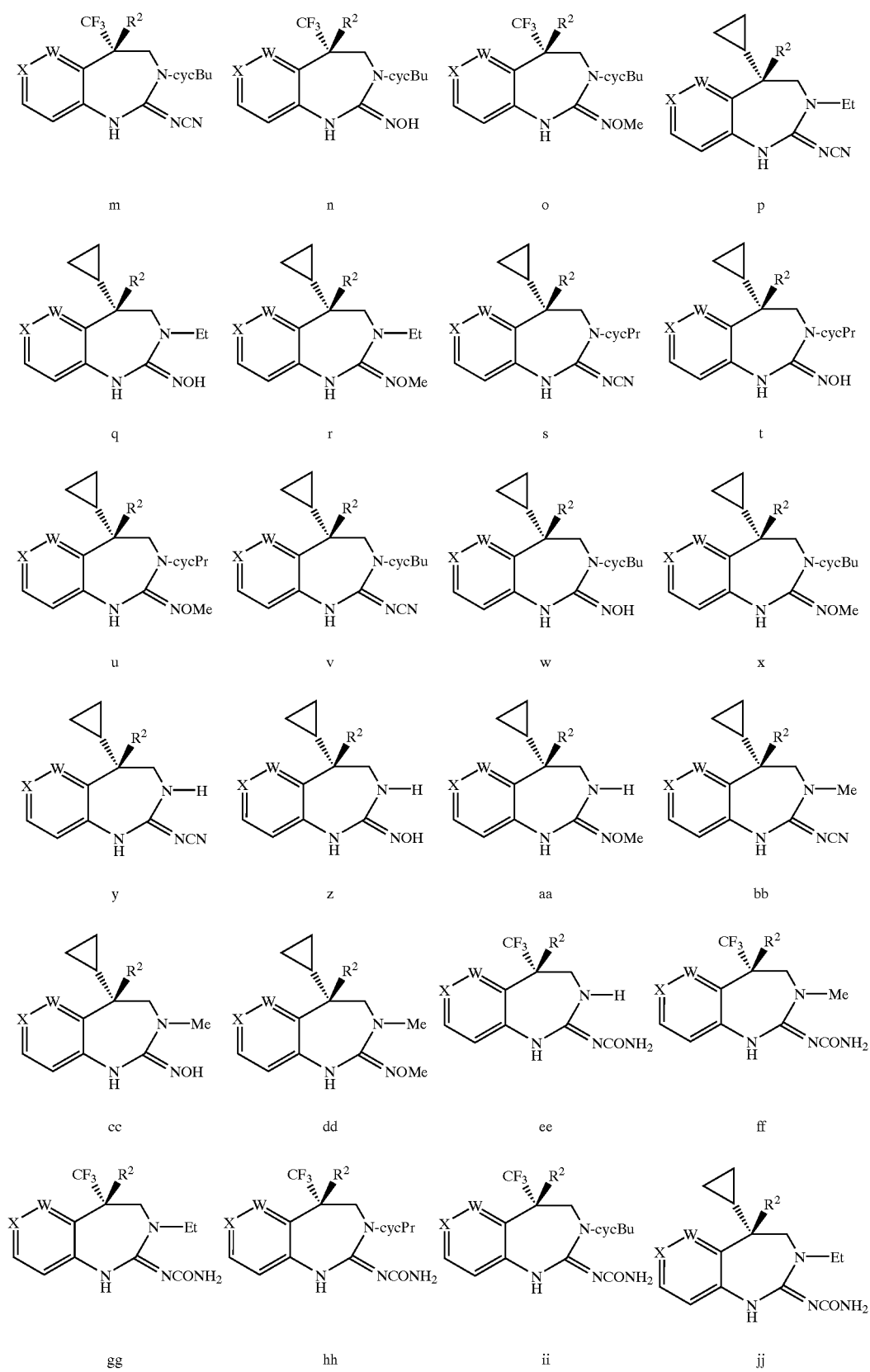

TABLE 2*-continued
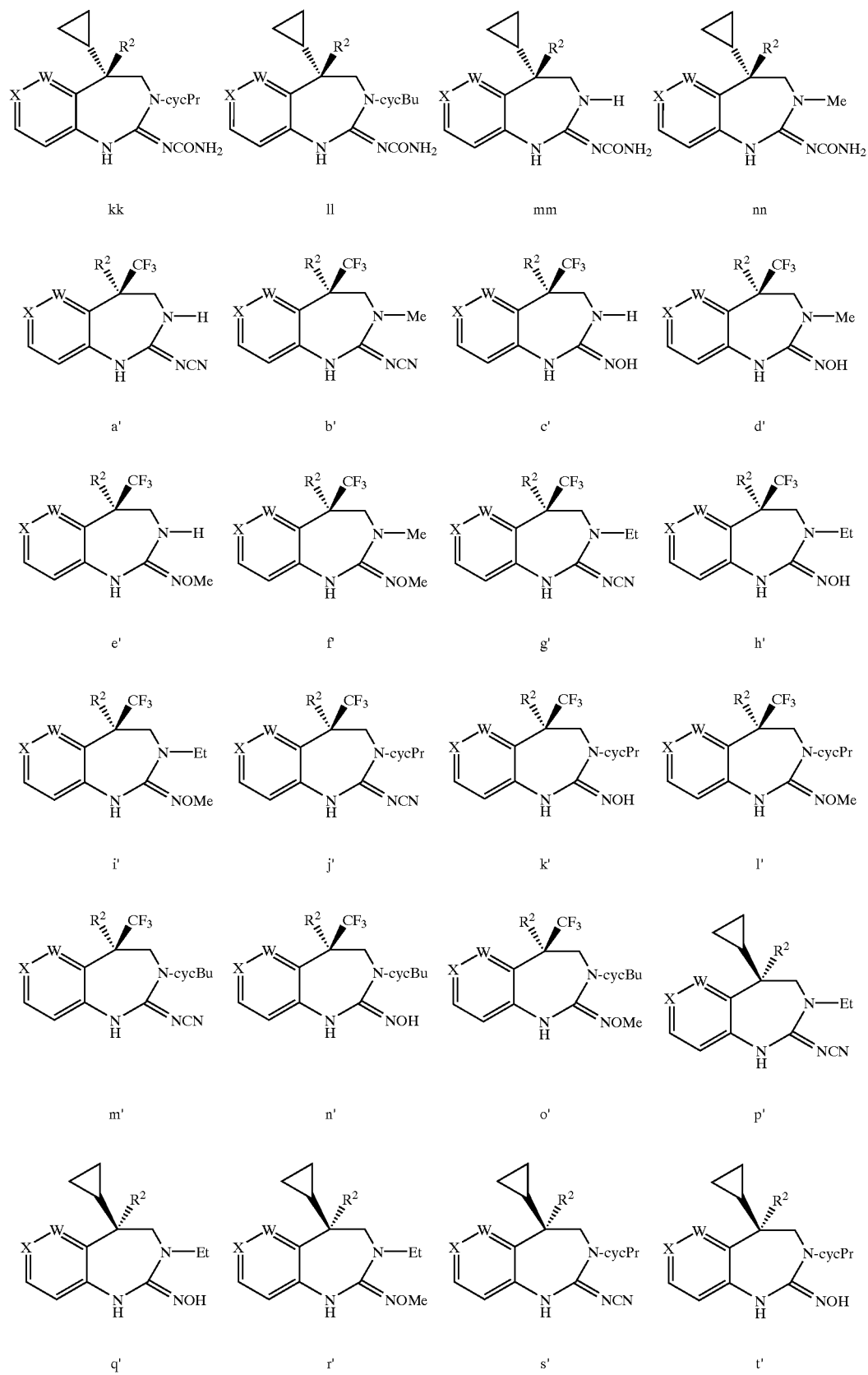

TABLE 2*-continued

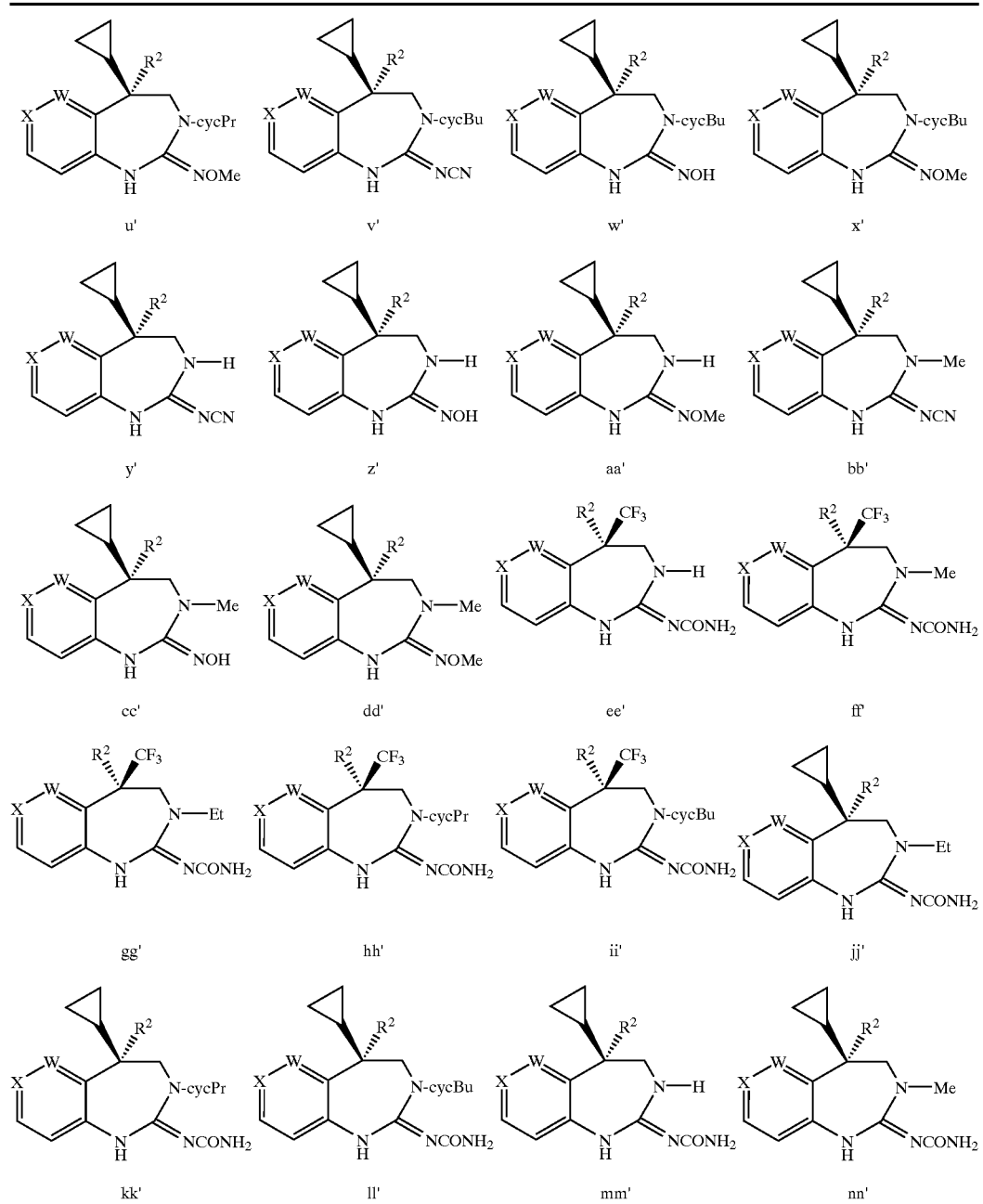

*Unless otherwise indicated, stereochemisty at each asymmetric center can be either R or S, or both cis and trans geometric isomers of a structure are intended unless a specific geometric isomer is indicated.

| Entry # | W  | X  | R$^2$            | Entry # | W  | X  | R$^2$              |
|---------|----|----|------------------|---------|----|----|--------------------|
| 1.      | CH | CH | C≡C-cycPr        | 9.      | CH | CH | C≡C-Me             |
| 2.      | CH | CH | C≡C-(1-CH$_3$-cycPr) | 10.     | CH | CH | C≡C-Ph             |
| 3.      | CH | CH | C≡C-iPr          | 11.     | CH | CH | C≡C-2-Pyridyl      |
| 4.      | CH | CH | C≡C-nPr          | 12.     | CH | CH | C≡C-3-Pyridyl      |
| 5.      | CH | CH | C≡C-Bu           | 13.     | CH | CH | C≡C-4-Pyridyl      |
| 6.      | CH | CH | C≡C-iBu          | 14.     | CH | CH | C≡C-2-furanyl      |
| 7.      | CH | CH | C≡C-tBu          | 15.     | CH | CH | C≡C-3-furanyl      |
| 8.      | CH | CH | C≡C-Et           | 16.     | CH | CH | C≡C-2-thienyl      |

| Entry # | W | X | R² |
|---|---|---|---|
| 17. | CH | CH | C≡C-3-thienyl |
| 18. | CH | CH | CH=CH-cycPr |
| 19. | CH | CH | CH=CH-iPr |
| 20. | CH | CH | CH=CH-nPr |
| 21. | CH | CH | CH=CH-Bu |
| 22. | CH | CH | CH=CH-iBu |
| 23. | CH | CH | CH=CH-tBu |
| 24. | CH | CH | CH=CH-Et |
| 25. | CH | CH | CH=CH-Me |
| 26. | CH | CH | CH=CH-Ph |
| 27. | CH | CH | CH=CH-2-Pyridyl |
| 28. | CH | CH | CH=CH-3-Pyridyl |
| 29. | CH | CH | CH=CH-4-Pyridyl |
| 30. | CH | CH | CH=CH-2-furanyl |
| 31. | CH | CH | CH=CH-3-furanyl |
| 32. | CH | CH | CH=CH-2-thienyl |
| 33. | CH | CH | CH=CH-3-thienyl |
| 34. | CH | CH | CH₂CH₂CH₂CH₂CH₃ |
| 35. | CH | CH | CH₂CH₂CH(CH₃)₂ |
| 36. | CH | CH | CH₂CH₂CH₂CH₃ |
| 37. | CH | CH | CH₂CH₂CH₃ |
| 38. | CH | CH | CH₂CH₂-cycPr |
| 39. | CH | CH | CH₂CH₂-(1-CH₃-cycPr) |
| 40. | CH | CH | CH₂CH₂-tBu |
| 41. | CH | CH | CH₂CH₂-cycBu |
| 42. | CH | CH | CH₂CH₂-(1-CH₃-cycBu) |
| 43. | CH | CH | CH₂CH₂-2-Pyridyl |
| 44. | CH | CH | CH₂CH₂-3-Pyridyl |
| 45. | CH | CH | CH₂CH₂-4-Pyridyl |
| 46. | CH | CH | CH₂CH₂-2-furanyl |
| 47. | CH | CH | CH₂CH₂-3-furanyl |
| 48. | CH | CH | CH₂CH₂-2-thienyl |
| 49. | CH | CH | CH₂CH₂-3-thienyl |
| 50. | CH | CH | CH₂C≡C-cycPr |
| 51. | CH | CH | CH₂C≡C-2-furanyl |
| 52. | CH | CH | CH₂CH=CH-cycPr |
| 53. | CH | CH | CH₂CH=CH-2-furanyl |
| 54. | CH | CH | CH=CHCH₂-cycPr |
| 55. | CH | CH | CH=CHCH₂-2-furanyl |
| 56. | CH | CH | OCH₂C=C(CH₃)₂ |
| 57. | CH | CH | E-OCH₂C=CHCH₃ |
| 58. | CH | CH | Z-OCH₂C=CHCH₃ |
| 59. | CH | CH | OCH₂CH₃ |
| 60. | CH | CH | OCH₂CH₂CH₃ |
| 61. | CH | CH | OCH₂C=C(Cl)₂ |
| 62. | CH | CH | OCH₂C=CH₂ |
| 63. | CH | CH | OCH₂C≡CCH₃ |
| 64. | CH | CH | OCH₂CH₂CH₃ |
| 65. | CH | CH | OCH₂-cycPr |
| 66. | CH | CH | OCH₂-(1-CH₃-cycPr) |
| 67. | CH | CH | OCH₂-cycBu |
| 68. | CH | CH | OCH₂-(1-CH₃-cycBu) |
| 69. | CH | CH | OCH₂-Phenyl |
| 70. | CH | CH | OCH₂CH₂-cycPr |
| 71. | CH | CH | OCH₂CH=cycPr |
| 72. | CCl | CH | C≡C-cycPr |
| 73. | CCl | CH | C≡C-(1-CH₃-cycPr) |
| 74. | CCl | CH | C≡C-iPr |
| 75. | CCl | CH | C≡C-nPr |
| 76. | CCl | CH | C≡C-Bu |
| 77. | CCl | CH | C≡C-iBu |
| 78. | CCl | CH | C≡C-tBu |
| 79. | CCl | CH | C≡C-Et |
| 80. | CCl | CH | C≡C-Me |
| 81. | CCl | CH | C≡C-Ph |
| 82. | CCl | CH | C≡C-2-Pyridyl |
| 83. | CCl | CH | C≡C-3-Pyridyl |
| 84. | CCl | CH | C≡C-4-Pyridyl |
| 85. | CCl | CH | C≡C-2-furanyl |
| 86. | CCl | CH | C≡C-3-furanyl |
| 87. | CCl | CH | C≡C-2-thienyl |
| 88. | CCl | CH | C≡C-3-thienyl |
| 89. | CCl | CH | CH=CH-cycPr |
| 90. | CCl | CH | CH=CH-iPr |
| 91. | CCl | CH | CH=CH-nPr |
| 92. | CCl | CH | CH=CH-Bu |
| 93. | CCl | CH | CH=CH-iBu |
| 94. | CCl | CH | CH=CH-tBu |
| 95. | CCl | CH | CH=CH-Et |
| 96. | CCl | CH | CH=CH-Me |
| 97. | CCl | CH | CH=CH-Ph |
| 98. | CCl | CH | CH=CH-2-Pyridyl |
| 99. | CCl | CH | CH=CH-3-Pyridyl |
| 100. | CCl | CH | CH=CH-4-Pyridyl |
| 101. | CCl | CH | CH=CH-2-furanyl |
| 102. | CCl | CH | CH=CH-3-furanyl |
| 103. | CCl | CH | CH=CH-2-thienyl |
| 104. | CCl | CH | CH=CH-3-thienyl |
| 105. | CCl | CH | CH₂CH₂CH₂CH₂CH₃ |
| 106. | CCl | CH | CH₂CH₂CH(CH₃)₂ |
| 107. | CCl | CH | CH₂CH₂CH₂CH₃ |
| 108. | CCl | CH | CH₂CH₂CH₃ |
| 109. | CCl | CH | CH₂CH₂-cycPr |
| 110. | CCl | CH | CH₂CH₂-(1-CH₃-cycPr) |
| 111. | CCl | CH | CH₂CH₂-tBu |
| 112. | CCl | CH | CH₂CH₂-cycBu |
| 113. | CCl | CH | CH₂CH₂-(1-CH₃-cycBu) |
| 114. | CCl | CH | CH₂CH₂-2-Pyridyl |
| 115. | CCl | CH | CH₂CH₂-3-Pyridyl |
| 116. | CCl | CH | CH₂CH₂-4-Pyridyl |
| 117. | CCl | CH | CH₂CH₂-2-furanyl |
| 118. | CCl | CH | CH₂CH₂-3-furanyl |
| 119. | CCl | CH | CH₂CH₂-2-thienyl |
| 120. | CCl | CH | CH₂CH₂-3-thienyl |
| 121. | CCl | CH | CH₂C≡C-cycPr |
| 122. | CCl | CH | CH₂C≡C-2-furanyl |
| 123. | CCl | CH | CH₂CH=CH-cycPr |
| 124. | CCl | CH | CH₂CH=CH-2-furanyl |
| 125. | CCl | CH | CH=CHCH₂-cycPr |
| 126. | CCl | CH | CH=CHCH₂-2-furanyl |
| 127. | CCl | CH | OCH₂C=C(CH₃)₂ |
| 128. | CCl | CH | E-CH₂C=C(CH₃)₂ |
| 129. | CCl | CH | Z-OCH₂C=CHCH₃ |
| 130. | CCl | CH | OCH₂CH₃ |
| 131. | CCl | CH | OCH₂CH₂CH₃ |
| 132. | CCl | CH | OCH₂C=C(Cl)₂ |
| 133. | CCl | CH | OCH₂C=CH₂ |
| 134. | CCl | CH | OCH₂C≡CCH₃ |
| 135. | CCl | CH | OCH₂CH₂CH₃ |
| 136. | CCl | CH | OCH₂-cycPr |
| 137. | CCl | CH | OCH₂-(1-CH₃-cycPr) |
| 138. | CCl | CH | OCH₂-cycBu |
| 139. | CCl | CH | OCH₂-(1-CH₃-cycBu) |
| 140. | CCl | CH | OCH₂-Phenyl |
| 141. | CCl | CH | OCH₂CH₂-cycPr |
| 142. | CCl | CH | OCH₂CH=cycPr |
| 143. | CH | CCl | C≡C-cycPr |
| 144. | CH | CCl | C≡C-(1-CH₃-cycPr) |
| 145. | CH | CCl | C≡C-iPr |
| 146. | CH | CCl | C≡C-nPr |
| 147. | CH | CCl | C≡C-Bu |
| 148. | CH | CCl | C≡C-iBu |
| 149. | CH | CCl | C≡C-tBu |
| 150. | CH | CCl | C≡C-Et |
| 151. | CH | CCl | C≡C-Me |
| 152. | CH | CCl | C≡C-Ph |
| 153. | CH | CCl | C≡C-2-Pyridyl |
| 154. | CH | CCl | C≡C-3-Pyridyl |
| 155. | CH | CCl | C≡C-4-Pyridyl |
| 156. | CH | CCl | C≡C-2-furanyl |
| 157. | CH | CCl | C≡C-3-furanyl |
| 158. | CH | CCl | C≡C-2-thienyl |
| 159. | CH | CCl | C≡C-3-thienyl |
| 160. | CH | CCl | CH=CH-cycPr |
| 161. | CH | CCl | CH=CH-iPr |
| 162. | CH | CCl | CH=CH-nPr |
| 163. | CH | CCl | CH=CH-Bu |
| 164. | CH | CCl | CH=CH-iBu |
| 165. | CH | CCl | CH=CH-tBu |
| 166. | CH | CCl | CH=CH-Et |
| 167. | CH | CCl | CH=CH-Me |
| 168. | CH | CCl | CH=CH-Ph |
| 169. | CH | CCl | CH=CH-2-Pyridyl |
| 170. | CH | CCl | CH=CH-3-Pyridyl |

-continued

| Entry # | W | X | R² |
|---|---|---|---|
| 171. | CH | CCl | CH=CH-4-Pyridyl |
| 172. | CH | CCl | CH=CH-2-furanyl |
| 173. | CH | CCl | CH=CH-3-furanyl |
| 174. | CH | CCl | CH=CH-2-thienyl |
| 175. | CH | CCl | CH=CH-3-thienyl |
| 176. | CH | CCl | CH$_2$CH$_2$CH$_2$CH$_2$CH$_3$ |
| 177. | CH | CCl | CH$_2$CH$_2$CH(CH$_3$)$_2$ |
| 178. | CH | CCl | CH$_2$CH$_2$CH$_2$CH$_3$ |
| 179. | CH | CCl | CH$_2$CH$_2$CH$_3$ |
| 180. | CH | CCl | CH$_2$CH$_2$-cycPr |
| 181. | CH | CCl | CH$_2$CH$_2$-(1-CH$_3$-cycPr) |
| 182. | CH | CCl | CH$_2$CH$_2$-tBu |
| 183. | CH | CCl | CH$_2$CH$_2$-cycBu |
| 184. | CH | CCl | CH$_2$CH$_2$-(1-CH$_3$-cycBu) |
| 185. | CH | CCl | CH$_2$CH$_2$-2-Pyridyl |
| 186. | CH | CCl | CH$_2$CH$_2$-3-Pyridyl |
| 187. | CH | CCl | CH$_2$CH$_2$-4-Pyridyl |
| 188. | CH | CCl | CH$_2$CH$_2$-2-furanyl |
| 189. | CH | CCl | CH$_2$CH$_2$-3-furanyl |
| 190. | CH | CCl | CH$_2$CH$_2$-2-thienyl |
| 191. | CH | CCl | CH$_2$CH$_2$-3-thienyl |
| 192. | CH | CCl | CH$_2$C≡C-cycPr |
| 193. | CH | CCl | CH$_2$C≡C-2-furanyl |
| 194. | CH | CCl | CH$_2$CH=CH-cycPr |
| 195. | CH | CCl | CH$_2$CH=CH-2-furanyl |
| 196. | CH | CCl | CH=CHCH$_2$-cycPr |
| 197. | CH | CCl | CH=CHCH$_2$-2-furanyl |
| 198. | CH | CCl | OCH$_2$C=C(CH$_3$)$_2$ |
| 199. | CH | CCl | E-OCH$_2$C=CHCH$_3$ |
| 200. | CH | CCl | Z-OCH$_2$C=CHCH$_3$ |
| 201. | CH | CCl | OCH$_2$CH$_3$ |
| 202. | CH | CCl | OCH$_2$CH$_2$CH$_3$ |
| 203. | CH | CCl | OCH$_2$C=C(Cl)$_2$ |
| 204. | CH | CCl | OCH$_2$C=CH$_2$ |
| 205. | CH | CCl | OCH$_2$C=CCH$_3$ |
| 206. | CH | CCl | OCH$_2$CH$_2$CH$_3$ |
| 207. | CH | CCl | OCH$_2$-cycPr |
| 208. | CH | CCl | OCH$_2$-(1-CH$_3$-cycPr) |
| 209. | CH | CCl | OCH$_2$-cycBu |
| 210. | CH | CCl | OCH$_2$-(1-CH$_3$-cycBu) |
| 211. | CH | CCl | OCH$_2$-Phenyl |
| 212. | CH | CCl | OCH$_2$CH$_2$-cycPr |
| 213. | CH | CCl | OCH$_2$CH=cycPr |
| 214. | CCl | CCl | C≡C-cycPr |
| 215. | CCl | CCl | C≡C-(1-CH$_3$-cycPr) |
| 216. | CCl | CCl | C≡C-iPr |
| 217. | CCl | CCl | C≡C-nPr |
| 218. | CCl | CCl | C≡C-Bu |
| 219. | CCl | CCl | C≡C-iBu |
| 220. | CCl | CCl | C≡C-tBu |
| 221. | CCl | CCl | C≡C-Et |
| 222. | CCl | CCl | C≡C-Me |
| 223. | CCl | CCl | C≡C-Ph |
| 224. | CCl | CCl | C≡C-2-Pyridyl |
| 225. | CCl | CCl | C≡C-3-Pyridyl |
| 226. | CCl | CCl | C≡C-4-Pyridyl |
| 227. | CCl | CCl | C≡C-2-furanyl |
| 228. | CCl | CCl | C≡C-3-furanyl |
| 229. | CCl | CCl | C≡C-2-thienyl |
| 230. | CCl | CCl | C≡C-3-thienyl |
| 231. | CCl | CCl | CH=CH-cycPr |
| 232. | CCl | CCl | CH=CH-iPr |
| 233. | CCl | CCl | CH=CH-nPr |
| 234. | CCl | CCl | CH=CH-Bu |
| 235. | CCl | CCl | CH=CH-iBu |
| 236. | CCl | CCl | CH=CH-tBu |
| 237. | CCl | CCl | CH=CH-Et |
| 238. | CCl | CCl | CH=CH-Me |
| 239. | CCl | CCl | CH=CH-Ph |
| 240. | CCl | CCl | CH=CH-2-Pyridyl |
| 241. | CCl | CCl | CH=CH-3-Pyridyl |
| 242. | CCl | CCl | CH=CH-4-Pyridyl |
| 243. | CCl | CCl | CH=CH-2-furanyl |
| 244. | CCl | CCl | CH=CH-3-furanyl |
| 245. | CCl | CCl | CH=CH-2-thienyl |
| 246. | CCl | CCl | CH=CH-3-thienyl |
| 247. | CCl | CCl | CH$_2$CH$_2$CH$_2$CH$_2$CH$_3$ |
| 248. | CCl | CCl | CH$_2$CH$_2$CH(CH$_3$)$_2$ |
| 249. | CCl | CCl | CH$_2$CH$_2$CH$_2$CH$_3$ |
| 250. | CCl | CCl | CH$_2$CH$_2$CH$_3$ |
| 251. | CCl | CCl | CH$_2$CH$_2$-cycPr |
| 252. | CCl | CCl | CH$_2$CH$_2$-(1-CH$_3$-cycPr) |
| 253. | CCl | CCl | CH$_2$CH$_2$-tBu |
| 254. | CCl | CCl | CH$_2$CH$_2$-cycBu |
| 255. | CCl | CCl | CH$_2$CH$_2$-(1-CH$_3$-cycBu) |
| 256. | CCl | CCl | CH$_2$CH$_2$-2-Pyridyl |
| 257. | CCl | CCl | CH$_2$CH$_2$-3-Pyridyl |
| 258. | CCl | CCl | CH$_2$CH$_2$-4-Pyridyl |
| 259. | CCl | CCl | CH$_2$CH$_2$-2-furanyl |
| 260. | CCl | CCl | CH$_2$CH$_2$-3-furanyl |
| 261. | CCl | CCl | CH$_2$CH$_2$-2-thienyl |
| 262. | CCl | CCl | CH$_2$CH$_2$-3-thienyl |
| 263. | CCl | CCl | CH$_2$C≡C-cycPr |
| 264. | CCl | CCl | CH$_2$C≡C-2-furanyl |
| 265. | CCl | CCl | CH$_2$CH=CH-cycPr |
| 266. | CCl | CCl | CH$_2$CH=CH-2-furanyl |
| 267. | CCl | CCl | CH=CHCH$_2$-cycPr |
| 268. | CCl | CCl | CH=CHCH$_2$-2-furanyl |
| 269. | CCl | CCl | OCH$_2$C=C(CH$_3$)$_2$ |
| 270. | CCl | CCl | E-OCH$_2$C=CHCH$_3$ |
| 271. | CCl | CCl | Z-OCH$_2$C=CHCH$_3$ |
| 272. | CCl | CCl | OCH$_2$CH$_3$ |
| 273. | CCl | CCl | OCH$_2$CH$_2$CH$_3$ |
| 274. | CCl | CCl | OCH$_2$C=C(Cl)$_2$ |
| 275. | CCl | CCl | OCH$_2$C=CH$_2$ |
| 276. | CCl | CCl | OCH$_2$C=CCH$_3$ |
| 277. | CCl | CCl | OCH$_2$CH$_2$CH$_3$ |
| 278. | CCl | CCl | OCH$_2$-cycPr |
| 279. | CCl | CCl | OCH$_2$-(1-CH$_3$-cycPr) |
| 280. | CCl | CCl | OCH$_2$-cycBu |
| 281. | CCl | CCl | OCH$_2$-(1-CH$_3$-cycBu) |
| 282. | CCl | CCl | OCH$_2$-Phenyl |
| 283. | CCl | CCl | OCH$_2$CH$_2$-cycPr |
| 284. | CCl | CCl | OCH$_2$CH=cycPr |
| 285. | CF | CH | C≡C-cycPr |
| 286. | CF | CH | C≡C-(1-CH$_3$-cycPr) |
| 287. | CF | CH | C≡C-iPr |
| 288. | CF | CH | C≡C-nPr |
| 289. | CF | CH | C≡C-Bu |
| 290. | CF | CH | C≡C-iBu |
| 291. | CF | CH | C≡C-tBu |
| 292. | CF | CH | C≡C-Et |
| 293. | CF | CH | C≡C-Me |
| 294. | CF | CH | C≡C-Ph |
| 295. | CF | CH | C≡C-2-Pyridyl |
| 296. | CF | CH | C≡C-3-Pyridyl |
| 297. | CF | CH | C≡C-4-Pyridyl |
| 298. | CF | CH | C≡C-2-furanyl |
| 299. | CF | CH | C≡C-3-furanyl |
| 300. | CF | CH | C≡C-2-thienyl |
| 301. | CF | CH | C≡C-3-thienyl |
| 302. | CF | CH | CH=CH-cycPr |
| 303. | CF | CH | CH=CH-iPr |
| 304. | CF | CH | CH=CH-nPr |
| 305. | CF | CH | CH=CH-Bu |
| 306. | CF | CH | CH=CH-iBu |
| 307. | CF | CH | CH=CH-tBu |
| 308. | CF | CH | CH=CH-Et |
| 309. | CF | CH | CH=CH-Me |
| 310. | CF | CH | CH=CH-Ph |
| 311. | CF | CH | CH=CH-2-Pyridyl |
| 312. | CF | CH | CH=CH-3-Pyridyl |
| 313. | CF | CH | CH=CH-4-Pyridyl |
| 314. | CF | CH | CH=CH-2-furanyl |
| 315. | CF | CH | CH=CH-3-furanyl |
| 316. | CF | CH | CH=CH-2-thienyl |
| 317. | CF | CH | CH=CH-3-thienyl |
| 318. | CF | CH | CH$_2$CH$_2$CH$_2$CH$_2$CH$_3$ |
| 319. | CF | CH | CH$_2$CH$_2$CH(CH$_3$)$_2$ |
| 320. | CF | CH | CH$_2$CH$_2$CH$_2$CH$_3$ |
| 321. | CF | CH | CH$_2$CH$_2$CH$_3$ |
| 322. | CF | CH | CH$_2$CH$_2$-cycPr |
| 323. | CF | CH | CH$_2$CH$_2$-(1-CH$_3$-cycPr) |
| 324. | CF | CH | CH$_2$CH$_2$-tBu |

-continued

| Entry # | W | X | R² |
|---|---|---|---|
| 325. | CF | CH | CH₂CH₂-cycBu |
| 326. | CF | CH | CH₂CH₂-(1-CH₃-cycBu) |
| 327. | CF | CH | CH₂CH₂-2-Pyridyl |
| 328. | CF | CH | CH₂CH₂-3-Pyridyl |
| 329. | CF | CH | CH₂CH₂-4-Pyridyl |
| 330. | CF | CH | CH₂CH₂-2-furanyl |
| 331. | CF | CH | CH₂CH₂-3-furanyl |
| 332. | CF | CH | CH₂CH₂-2-thienyl |
| 333. | CF | CH | CH₂CH₂-3-thienyl |
| 334. | CF | CH | CH₂C≡C-cycPr |
| 335. | CF | CH | CH₂C≡C-2-furanyl |
| 336. | CF | CH | CH₂CH═CH-cycPr |
| 337. | CF | CH | CH₂CH═CH-2-furanyl |
| 338. | CF | CH | CH═CHCH₂-cycPr |
| 339. | CF | CH | CH═CHCH₂-2-furanyl |
| 340. | CF | CH | OCH₂C═C(CH₃)₂ |
| 341. | CF | CH | E-OCH₂C═CHCH₃ |
| 342. | CF | CH | Z-OCH₂C═CHCH₃ |
| 343. | CF | CH | OCH₂CH₃ |
| 344. | CF | CH | OCH₂CH₂CH₃ |
| 345. | CF | CH | OCH₂C═C(Cl)₂ |
| 346. | CF | CH | OCH₂C═CH₂ |
| 347. | CF | CH | OCH₂C≡CCH₃ |
| 348. | CF | CH | OCH₂CH₂CH₃ |
| 349. | CF | CH | OCH₂-cycPr |
| 350. | CF | CH | OCH₂-(1-CH₃-cycPr) |
| 351. | CF | CH | OCH₂-cycBu |
| 352. | CF | CH | OCH₂-(1-CH₃-cycBu) |
| 353. | CF | CH | OCH₂-Phenyl |
| 354. | CF | CH | OCH₂CH₂-cycPr |
| 355. | CF | CH | OCH₂CH═cycPr |
| 356. | CH | CF | C≡C-cycPr |
| 357. | CH | CF | C≡C-(1-CH₃-cycPr) |
| 358. | CH | CF | C≡C-iPr |
| 359. | CH | CF | C≡C-nPr |
| 360. | CH | CF | C≡C-Bu |
| 361. | CH | CF | C≡C-iBu |
| 362. | CH | CF | C≡C-tBu |
| 363. | CH | CF | C≡C-Et |
| 364. | CH | CF | C≡C-Me |
| 365. | CH | CF | C≡C-Ph |
| 366. | CH | CF | C≡C-2-Pyridyl |
| 367. | CH | CF | C≡C-3-Pyridyl |
| 368. | CH | CF | C≡C-4-Pyridyl |
| 369. | CH | CF | C≡C-2-furanyl |
| 370. | CH | CF | C≡C-3-furanyl |
| 371. | CH | CF | C≡C-2-thienyl |
| 372. | CH | CF | C≡C-3-thienyl |
| 373. | CH | CF | CH═CH-cycPr |
| 374. | CH | CF | CH═CH-iPr |
| 375. | CH | CF | CH═CH-nPr |
| 376. | CH | CF | CH═CH-Bu |
| 377. | CH | CF | CH═CH-iBu |
| 378. | CH | CF | CH═CH-tBu |
| 379. | CH | CF | CH═CH-Et |
| 380. | CH | CF | CH═CH-Me |
| 381. | CH | CF | CH═CH-Ph |
| 382. | CH | CF | CH═CH-2-Pyridyl |
| 383. | CH | CF | CH═CH-3-Pyridyl |
| 384. | CH | CF | CH═CH-4-Pyridyl |
| 385. | CH | CF | CH═CH-2-furanyl |
| 386. | CH | CF | CH═CH-3-furanyl |
| 387. | CH | CF | CH═CH-2-thienyl |
| 388. | CH | CF | CH═CH-3-thienyl |
| 389. | CH | CF | CH₂CH₂CH₂CH₂CH₃ |
| 390. | CH | CF | CH₂CH₂CH(CH₃)₂ |
| 391. | CH | CF | CH₂CH₂CH₂CH₃ |
| 392. | CH | CF | CH₂CH₂CH₃ |
| 393. | CH | CF | CH₂CH₂-cycPr |
| 394. | CH | CF | CH₂CH₂-(1-CH₃-cycPr) |
| 395. | CH | CF | CH₂CH₂-tBu |
| 396. | CH | CF | CH₂CH₂-cycBu |
| 397. | CH | CF | CH₂CH₂-(1-CH₃-cycBu) |
| 398. | CH | CF | CH₂CH₂-2-Pyridyl |
| 399. | CH | CF | CH₂CH₂-3-Pyridyl |
| 400. | CH | CF | CH₂CH₂-4-Pyridyl |
| 401. | CH | CF | CH₂CH₂-2-furanyl |
| 402. | CH | CF | CH₂CH₂-3-furanyl |
| 403. | CH | CF | CH₂CH₂-2-thienyl |
| 404. | CH | CF | CH₂CH₂-3-thienyl |
| 405. | CH | CF | CH₂C≡C-cycPr |
| 406. | CH | CF | CH₂C≡C-2-furanyl |
| 407. | CH | CF | CH₂CH═CH-cycPr |
| 408. | CH | CF | CH₂CH═CH-2-furanyl |
| 409. | CH | CF | CH═CHCH₂-cycPr |
| 410. | CH | CF | CH═CHCH₂-2-furanyl |
| 411. | CH | CF | OCH₂C═C(CH₃)₂ |
| 412. | CH | CF | E-OCH₂C═CHCH₃ |
| 413. | CH | CF | Z-OCH₂C═CHCH₃ |
| 414. | CH | CF | OCH₂CH₃ |
| 415. | CH | CF | OCH₂CH₂CH₃ |
| 416. | CH | CF | OCH₂C═C(Cl)₂ |
| 417. | CH | CF | OCH₂C═CH₂ |
| 418. | CH | CF | OCH₂C≡CCH₃ |
| 419. | CH | CF | OCH₂CH₂CH₃ |
| 420. | CH | CF | OCH₂-cycPr |
| 421. | CH | CF | OCH₂-(1-CH₃-cycPr) |
| 422. | CH | CF | OCH₂-cycBu |
| 423. | CH | CF | OCH₂-(1-CH₃-cycBu) |
| 424. | CH | CF | OCH₂-Phenyl |
| 425. | CH | CF | OCH₂CH₂-cycPr |
| 426. | CH | CF | OCH₂CH═cycPr |
| 427. | CF | CF | C≡C-cycPr |
| 428. | CF | CF | C≡C-(1-CH₃-cycPr) |
| 429. | CF | CF | C≡C-iPr |
| 430. | CF | CF | C≡C-nPr |
| 431. | CF | CF | C≡C-Bu |
| 432. | CF | CF | C≡C-iBu |
| 433. | CF | CF | C≡C-tBu |
| 434. | CF | CF | C≡C-Et |
| 435. | CF | CF | C≡C-Me |
| 436. | CF | CF | C≡C-Ph |
| 437. | CF | CF | C≡C-2-Pyridyl |
| 438. | CF | CF | C≡C-3-Pyridyl |
| 439. | CF | CF | C≡C-4-Pyridyl |
| 440. | CF | CF | C≡C-2-furanyl |
| 441. | CF | CF | C≡C-3-furanyl |
| 442. | CF | CF | C≡C-2-thienyl |
| 443. | CF | CF | C≡C-3-thienyl |
| 444. | CF | CF | CH═CH-cycPr |
| 445. | CF | CF | CH═CH-iPr |
| 446. | CF | CF | CH═CH-nPr |
| 447. | CF | CF | CH═CH-Bu |
| 448. | CF | CF | CH═CH-iBu |
| 449. | CF | CF | CH═CH-tBu |
| 450. | CF | CF | CH═CH-Et |
| 451. | CF | CF | CH═CH-Me |
| 452. | CF | CF | CH═CH-Ph |
| 453. | CF | CF | CH═CH-2-Pyridyl |
| 454. | CF | CF | CH═CH-3-Pyridyl |
| 455. | CF | CF | CH═CH-4-Pyridyl |
| 456. | CF | CF | CH═CH-2-furanyl |
| 457. | CF | CF | CH═CH-3-furanyl |
| 458. | CF | CF | CH═CH-2-thienyl |
| 459. | CF | CF | CH═CH-3-thienyl |
| 460. | CF | CF | CH₂CH₂CH₂CH₂CH₃ |
| 461. | CF | CF | CH₂CH₂CH(CH₃)₂ |
| 462. | CF | CF | CH₂CH₂CH₂CH₃ |
| 463. | CF | CF | CH₂CH₂CH₃ |
| 464. | CF | CF | CH₂CH₂-cycPr |
| 465. | CF | CF | CH₂CH₂-(1-CH₃-cycPr) |
| 466. | CF | CF | CH₂CH₂-tBu |
| 467. | CF | CF | CH₂CH₂-cycBu |
| 468. | CF | CF | CH₂CH₂-(1-CH₃-cycBu) |
| 469. | CF | CF | CH₂CH₂-2-Pyridyl |
| 470. | CF | CF | CH₂CH₂-3-Pyridyl |
| 471. | CF | CF | CH₂CH₂-4-Pyridyl |
| 472. | CF | CF | CH₂CH₂-2-furanyl |
| 473. | CF | CF | CH₂CH₂-3-furanyl |
| 474. | CF | CF | CH₂CH₂-2-thienyl |
| 475. | CF | CF | CH₂CH₂-3-thienyl |
| 476. | CF | CF | CH₂C≡C-cycPr |
| 477. | CF | CF | CH₂C≡C-2-furanyl |
| 478. | CF | CF | CH₂CH═CH-cycPr |

-continued

| Entry # | W | X | R² |
|---|---|---|---|
| 479. | CF | CF | CH₂CH=CH-2-furanyl |
| 480. | CF | CF | CH=CHCH₂-cycPr |
| 481. | CF | CF | CH=CHCH₂-2-furanyl |
| 482. | CF | CF | OCH₂C=C(CH₃)₂ |
| 483. | CF | CF | E-OCH₂C=CHCH₃ |
| 484. | CF | CF | Z-OCH₂C=CHCH₃ |
| 485. | CF | CF | OCH₂CH₃ |
| 486. | CF | CF | OCH₂CH₂CH₃ |
| 487. | CF | CF | OCH₂C=C(Cl)₂ |
| 488. | CF | CF | OCH₂C=CH₂ |
| 489. | CF | CF | OCH₂C≡CCH₃ |
| 490. | CF | CF | OCH₂CH₂CH₃ |
| 491. | CF | CF | OCH₂-cycPr |
| 492. | CF | CF | OCH₂-(1-CH₃-cycPr) |
| 493. | CF | CF | OCH₂-cycBu |
| 494. | CF | CF | OCH₂-(1-CH₃-cycBu) |
| 495. | CF | CF | OCH₂-Phenyl |
| 496. | CF | CF | OCH₂CH₂-cycPr |
| 497. | CF | CF | OCH₂CH=cycPr |
| 498. | CCl | CF | C≡C-cycPr |
| 499. | CCl | CF | C≡C-(1-CH₃-cycPr) |
| 500. | CCl | CF | C≡C-iPr |
| 501. | CCl | CF | C≡C-nPr |
| 502. | CCl | CF | C≡C-Bu |
| 503. | CCl | CF | C≡C-iBu |
| 504. | CCl | CF | C≡C-tBu |
| 505. | CCl | CF | C≡C-Et |
| 506. | CCl | CF | C≡C-Me |
| 507. | CCl | CF | C≡C-Ph |
| 508. | CCl | CF | C≡C-2-Pyridyl |
| 509. | CCl | CF | C≡C-3-Pyridyl |
| 510. | CCl | CF | C≡C-4-Pyridyl |
| 511. | CCl | CF | C≡C-2-furanyl |
| 512. | CCl | CF | C≡C-3-furanyl |
| 513. | CCl | CF | C≡C-2-thienyl |
| 514. | CCl | CF | C≡C-3-thienyl |
| 515. | CCl | CF | CH=CH-cycPr |
| 516. | CCl | CF | CH=CH-iPr |
| 517. | CCl | CF | CH=CH-nPr |
| 518. | CCl | CF | CH=CH-Bu |
| 519. | CCl | CF | CH=CH-iBu |
| 520. | CCl | CF | CH=CH-tBu |
| 521. | CCl | CF | CH=CH-Et |
| 522. | CCl | CF | CH=CH-Me |
| 523. | CCl | CF | CH=CH-Ph |
| 524. | CCl | CF | CH=CH-2-Pyridyl |
| 525. | CCl | CF | CH=CH-3-Pyridyl |
| 526. | CCl | CF | CH=CH-4-Pyridyl |
| 527. | CCl | CF | CH=CH-2-furanyl |
| 528. | CCl | CF | CH=CH-3-furanyl |
| 529. | CCl | CF | CH=CH-2-thienyl |
| 530. | CCl | CF | CH=CH-3-thienyl |
| 531. | CCl | CF | CH₂CH₂CH₂CH₂CH₃ |
| 532. | CCl | CF | CH₂CH₂CH(CH₃)₂ |
| 533. | CCl | CF | CH₂CH₂CH₂CH₃ |
| 534. | CCl | CF | CH₂CH₂CH₃ |
| 535. | CCl | CF | CH₂CH₂-cycPr |
| 536. | CCl | CF | CH₂CH₂-(1-CH₃-cycPr) |
| 537. | CCl | CF | CH₂CH₂-tBu |
| 538. | CCl | CF | CH₂CH₂-cycBu |
| 539. | CCl | CF | CH₂CH₂-(1-CH₃-cycBu) |
| 540. | CCl | CF | CH₂CH₂-2-Pyridyl |
| 541. | CCl | CF | CH₂CH₂-3-Pyridyl |
| 542. | CCl | CF | CH₂CH₂-4-Pyridyl |
| 543. | CCl | CF | CH₂CH₂-2-furanyl |
| 544. | CCl | CF | CH₂CH₂-3-furanyl |
| 545. | CCl | CF | CH₂CH₂-2-thienyl |
| 546. | CCl | CF | CH₂CH₂-3-thienyl |
| 547. | CCl | CF | CH₂C≡C-cycPr |
| 548. | CCl | CF | CH₂C≡C-2-furanyl |
| 549. | CCl | CF | CH₂CH=CH-cycPr |
| 550. | CCl | CF | CH₂CH=CH-2-furanyl |
| 551. | CCl | CF | CH=CHCH₂-cycPr |
| 552. | CCl | CF | CH=CHCH₂-2-furanyl |
| 553. | CCl | CF | OCH₂C=C(CH₃)₂ |
| 554. | CCl | CF | E-OCH₂C=CHCH₃ |
| 555. | CCl | CF | Z-OCH₂C=CHCH₃ |
| 556. | CCl | CF | OCH₂CH₃ |
| 557. | CCl | CF | OCH₂CH₂CH₃ |
| 558. | CCl | CF | OCH₂C=C(Cl)₂ |
| 559. | CCl | CF | OCH₂C=CH₂ |
| 560. | CCl | CF | OCH₂C≡CCH₃ |
| 561. | CCl | CF | OCH₂CH₂CH₃ |
| 562. | CCl | CF | OCH₂-cycPr |
| 563. | CCl | CF | OCH₂-(1-CH₃-cycPr) |
| 564. | CCl | CF | OCH₂-cycBu |
| 565. | CCl | CF | OCH₂-(1-CH₃-cycBu) |
| 566. | CCl | CF | OCH₂-Phenyl |
| 567. | CCl | CF | OCH₂CH₂-cycPr |
| 568. | CCl | CF | OCH₂CH=cycPr |
| 569. | CF | CCl | C≡C-cycPr |
| 570. | CF | CCl | C≡C-(1-CH₃-cycPr) |
| 571. | CF | CCl | C≡C-iPr |
| 572. | CF | CCl | C≡C-nPr |
| 573. | CF | CCl | C≡C-Bu |
| 574. | CF | CCl | C≡C-iBu |
| 575. | CF | CCl | C≡C-tBu |
| 576. | CF | CCl | C≡C-Et |
| 577. | CF | CCl | C≡C-Me |
| 578. | CF | CCl | C≡C-Ph |
| 579. | CF | CCl | C≡C-2-Pyridyl |
| 580. | CF | CCl | C≡C-3-Pyridyl |
| 581. | CF | CCl | C≡C-4-Pyridyl |
| 582. | CF | CCl | C≡C-2-furanyl |
| 583. | CF | CCl | C≡C-3-furanyl |
| 584. | CF | CCl | C≡C-2-thienyl |
| 585. | CF | CCl | C≡C-3-thienyl |
| 586. | CF | CCl | CH=CH-cycPr |
| 587. | CF | CCl | CH=CH-iPr |
| 588. | CF | CCl | CH=CH-nPr |
| 589. | CF | CCl | CH=CH-Bu |
| 590. | CF | CCl | CH=CH-iBu |
| 591. | CF | CCl | CH=CH-tBu |
| 592. | CF | CCl | CH=CH-Et |
| 593. | CF | CCl | CH=CH-Me |
| 594. | CF | CCl | CH=CH-Ph |
| 595. | CF | CCl | CH=CH-2-Pyridyl |
| 596. | CF | CCl | CH=CH-3-Pyridyl |
| 597. | CF | CCl | CH=CH-4-Pyridyl |
| 598. | CF | CCl | CH=CH-2-furanyl |
| 599. | CF | CCl | CH=CH-3-furanyl |
| 600. | CF | CCl | CH=CH-2-thienyl |
| 601. | CF | CCl | CH=CH-3-thienyl |
| 602. | CF | CCl | CH₂CH₂CH₂CH₂CH₃ |
| 603. | CF | CCl | CH₂CH₂CH(CH₃)2 |
| 604. | CF | CCl | CH₂CH₂CH₂CH₃ |
| 605. | CF | CCl | CH₂CH₂CH₃ |
| 606. | CF | CCl | CH₂CH₂-cycPr |
| 607. | CF | CCl | CH₂CH₂-(1-CH₃-cycPr) |
| 608. | CF | CCl | CH₂CH₂-tBu |
| 609. | CF | CCl | CH₂CH₂-cycBu |
| 610. | CF | CCl | CH₂CH₂-(1-CH₃-cycBu) |
| 611. | CF | CCl | CH₂CH₂-2-Pyridyl |
| 612. | CF | CCl | CH₂CH₂-3-Pyridyl |
| 613. | CF | CCl | CH₂CH₂-4-Pyridyl |
| 614. | CF | CCl | CH₂CH₂-2-furanyl |
| 615. | CF | CCl | CH₂CH₂-3-furanyl |
| 616. | CF | CCl | CH₂CH₂-2-thienyl |
| 617. | CF | CCl | CH₂CH₂-3-thienyl |
| 618. | CF | CCl | CH₂C≡C-cycPr |
| 619. | CF | CCl | CH₂C≡C-2-furanyl |
| 620. | CF | CCl | CH₂CH=CH-cycPr |
| 621. | CF | CCl | CH₂CH=CH-2-furanyl |
| 622. | CF | CCl | CH=CHCH₂-cycPr |
| 623. | CF | CCl | CH=CHCH₂-2-furanyl |
| 624. | CF | CCl | OCH₂C=C(CH₃)₂ |
| 625. | CF | CCl | E-OCH₂C=CHCH₃ |
| 626. | CF | CCl | Z-OCH₂C=CHCH₃ |
| 627. | CF | CCl | OCH₂CH₃ |
| 628. | CF | CCl | OCH₂CH₂CH₃ |
| 629. | CF | CCl | OCH₂C=C(Cl)₂ |
| 630. | CF | CCl | OCH₂C=CH₂ |
| 631. | CF | CCl | OCH₂C≡CCH₃ |
| 632. | CF | CCl | OCH₂CH₂CH₃ |

-continued

| Entry # | W | X | R² |
|---|---|---|---|
| 633. | CF | CCl | OCH₂-cycPr |
| 634. | CF | CCl | OCH₂-(1-CH₃-cycPr) |
| 635. | CF | CCl | OCH₂-cycBu |
| 636. | CF | CCl | OCH₂-(1-CH₃-cycBu) |
| 637. | CF | CCl | OCH₂-Phenyl |
| 638. | CF | CCl | OCH₂CH₂-cycPr |
| 639. | CF | CCl | OCH₂CH=cycPr |
| 640. | C(OMe) | CH | C≡C-cycPr |
| 641. | C(OMe) | CH | C≡C-(1-CH₃-cycPr) |
| 642. | C(OMe) | CH | C≡C-iPr |
| 643. | C(OMe) | CH | C≡C-nPr |
| 644. | C(OMe) | CH | C≡C-Bu |
| 645. | C(OMe) | CH | C≡C-iBu |
| 646. | C(OMe) | CH | C≡C-tBu |
| 647. | C(OMe) | CH | C≡C-Et |
| 648. | C(OMe) | CH | C≡C-Me |
| 649. | C(OMe) | CH | C≡C-Ph |
| 650. | C(OMe) | CH | C≡C-2-Pyridyl |
| 651. | C(OMe) | CH | C≡C-3-Pyridyl |
| 652. | C(OMe) | CH | C≡C-4-Pyridyl |
| 653. | C(OMe) | CH | C≡C-2-furanyl |
| 654. | C(OMe) | CH | C≡C-3-furanyl |
| 655. | C(OMe) | CH | C≡C-2-thienyl |
| 656. | C(OMe) | CH | C≡C-3-thienyl |
| 657. | C(OMe) | CH | CH=CH-cycPr |
| 658. | C(OMe) | CH | CH=CH-iPr |
| 659. | C(OMe) | CH | CH=CH-npr |
| 660. | C(OMe) | CH | CH=CH-Bu |
| 661. | C(OMe) | CH | CH=CH-iBu |
| 662. | C(OMe) | CH | CH=CH-tBu |
| 663. | C(OMe) | CH | CH=CH-Et |
| 664. | C(OMe) | CH | CH=CH-Me |
| 665. | C(OMe) | CH | CH=CH-Ph |
| 666. | C(OMe) | CH | CH=CH-2-Pyridyl |
| 667. | C(OMe) | CH | CH=CH-3-Pyridyl |
| 668. | C(OMe) | CH | CH=CH-4-Pyridyl |
| 669. | C(OMe) | CH | CH=CH-2-furanyl |
| 670. | C(OMe) | CH | CH=CH-3-furanyl |
| 671. | C(OMe) | CH | CH=CH-2-thienyl |
| 672. | C(OMe) | CH | CH=CH-3-thienyl |
| 673. | C(OMe) | CH | CH₂CH₂CH₂CH₂CH₃ |
| 674. | C(OMe) | CH | CH₂CH₂CH(CH₃)₂ |
| 675. | C(OMe) | CH | CH₂CH₂CH₂CH₃ |
| 676. | C(OMe) | CH | CH₂CH₂CH₃ |
| 677. | C(OMe) | CH | CH₂CH₂-cycPr |
| 678. | C(OMe) | CH | CH₂CH₂-(1-CH₃-cycPr) |
| 679. | C(OMe) | CH | CH₂CH₂-tBu |
| 680. | C(OMe) | CH | CH₂CH₂-cycBu |
| 681. | C(OMe) | CH | CH₂CH₂-(1-CH₃-cycBu) |
| 682. | C(OMe) | CH | CH₂CH₂-2-Pyridyl |
| 683. | C(OMe) | CH | CH₂CH₂-3-Pyridyl |
| 684. | C(OMe) | CH | CH₂CH₂-4-Pyridyl |
| 685. | C(OMe) | CH | CH₂CH₂-2-furanyl |
| 686. | C(OMe) | CH | CH₂CH₂-3-furanyl |
| 687. | C(OMe) | CH | CH₂CH₂-2-thienyl |
| 688. | C(OMe) | CH | CH₂CH₂-3-thienyl |
| 689. | C(OMe) | CH | CH₂C≡C-cycPr |
| 690. | C(OMe) | CH | CH₂C≡C-2-furanyl |
| 691. | C(OMe) | CH | CH₂CH=CH-cycPr |
| 692. | C(OMe) | CH | CH₂CH=CH-2-furanyl |
| 693. | C(OMe) | CH | CH=CHCH₂-cycPr |
| 694. | C(OMe) | CH | CH=CHCH₂-2-furanyl |
| 695. | C(OMe) | CH | OCH₂C=C(CH₃)₂ |
| 696. | C(OMe) | CH | E-OCH₂C=CHCH₃ |
| 697. | C(OMe) | CH | Z-OCH₂C=CHCH₃ |
| 698. | C(OMe) | CH | OCH₂CH₃ |
| 699. | C(OMe) | CH | OCH₂CH₂CH₃ |
| 700. | C(OMe) | CH | OCH₂C=C(Cl)₂ |
| 701. | C(OMe) | CH | OCH₂C=CH₂ |
| 702. | C(OMe) | CH | OCH₂C≡CCH₃ |
| 703. | C(OMe) | CH | OCH₂CH₂CH₃ |
| 704. | C(OMe) | CH | OCH₂-cycPr |
| 705. | C(OMe) | CH | OCH₂-(1-CH₃-cycPr) |
| 706. | C(OMe) | CH | OCH₂-cycBu |
| 707. | C(OMe) | CH | OCH₂-(1-CH₃-cycBu) |
| 708. | C(OMe) | CH | OCH₂-Phenyl |
| 709. | C(OMe) | CH | OCH₂CH₂-cycPr |
| 710. | C(OMe) | CH | OCH₂CH=cycPr |
| 711. | CH | C(OMe) | C≡C-cycPr |
| 712. | CH | C(OMe) | C≡C-(1-CH₃-cycPr) |
| 713. | CH | C(OMe) | C≡C-iPr |
| 714. | CH | C(OMe) | C≡C-nPr |
| 715. | CH | C(OMe) | C≡C-Bu |
| 716. | CH | C(OMe) | C≡C-iBu |
| 717. | CH | C(OMe) | C≡C-tBu |
| 718. | CH | C(OMe) | C≡C-Et |
| 719. | CH | C(OMe) | C≡C-Me |
| 720. | CH | C(OMe) | C≡C-Ph |
| 721. | CH | C(OMe) | C≡C-2-Pyridyl |
| 722. | CH | C(OMe) | C≡C-3-Pyridyl |
| 723. | CH | C(OMe) | C≡C-4-Pyridyl |
| 724. | CH | C(OMe) | C≡C-2-furanyl |
| 725. | CH | C(OMe) | C≡C-3-furanyl |
| 726. | CH | C(OMe) | C≡C-2-thienyl |
| 727. | CH | C(OMe) | C≡C-3-thienyl |
| 728. | CH | C(OMe) | CH=CH-cycPr |
| 729. | CH | C(OMe) | CH=CH-iPr |
| 730. | CH | C(OMe) | CH=CH-nPr |
| 731. | CH | C(OMe) | CH=CH-Bu |
| 732. | CH | C(OMe) | CH=CH-iBu |
| 733. | CH | C(OMe) | CH=CH-tBu |
| 734. | CH | C(OMe) | CH=CH-Et |
| 735. | CH | C(OMe) | CH=CH-Me |
| 736. | CH | C(OMe) | CH=CH-Ph |
| 737. | CH | C(OMe) | CH=CH-2-Pyridyl |
| 738. | CH | C(OMe) | CH=CH-3-Pyridyl |
| 739. | CH | C(OMe) | CH=CH-4-Pyridyl |
| 740. | CH | C(OMe) | CH=CH-2-furanyl |
| 741. | CH | C(OMe) | CH=CH-3-furanyl |
| 742. | CH | C(OMe) | CH=CH-2-thienyl |
| 743. | CH | C(OMe) | CH=CH-3-thienyl |
| 744. | CH | C(OMe) | CH₂CH₂CH₂CH₂CH₃ |
| 745. | CH | C(OMe) | CH₂CH₂CH(CH₃)₂ |
| 746. | CH | C(OMe) | CH₂CH₂CH₂CH₃ |
| 747. | CH | C(OMe) | CH₂CH₂CH₃ |
| 748. | CH | C(OMe) | CH₂CH₂-cycPr |
| 749. | CH | C(OMe) | CH₂CH₂-(1-CH₃-cycPr) |
| 750. | CH | C(OMe) | CH₂CH₂-tBu |
| 751. | CH | C(OMe) | CH₂CH₂-cycBu |
| 752. | CH | C(OMe) | CH₂CH₂-(1-CH₃-cycBu) |
| 753. | CH | C(OMe) | CH₂CH₂-2-Pyridyl |
| 754. | CH | C(OMe) | CH₂CH₂-3-Pyridyl |
| 755. | CH | C(OMe) | CH₂CH₂-4-Pyridyl |
| 756. | CH | C(OMe) | CH₂CH₂-2-furanyl |
| 757. | CH | C(OMe) | CH₂CH₂-3-furanyl |
| 758. | CH | C(OMe) | CH₂CH₂-2-thienyl |
| 759. | CH | C(OMe) | CH₂CH₂-3-thienyl |
| 760. | CH | C(OMe) | CH₂C≡C-cycPr |
| 761. | CH | C(OMe) | CH₂C≡C-2-furanyl |
| 762. | CH | C(OMe) | CH₂CH=CH-cycPr |
| 763. | CH | C(OMe) | CH₂CH=CH-2-furanyl |
| 764. | CH | C(OMe) | CH=CHCH₂-cycPr |
| 765. | CH | C(OMe) | CH=CHCH₂-2-furanyl |
| 766. | CH | C(OMe) | OCH₂C=C(CH₃)₂ |
| 767. | CH | C(OMe) | E-OCH₂C=CHCH₃ |
| 768. | CH | C(OMe) | Z-OCH₂C=CHCH₃ |
| 769. | CH | C(OMe) | OCH₂CH₃ |
| 770. | CH | C(OMe) | OCH₂CH₂CH₃ |
| 771. | CH | C(OMe) | OCH₂C=C(Cl)₂ |
| 772. | CH | C(OMe) | OCH₂C=CH₂ |
| 773. | CH | C(OMe) | OCH₂C≡CCH₃ |
| 774. | CH | C(OMe) | OCH₂CH₂CH₃ |
| 775. | CH | C(OMe) | OCH₂-cycPr |
| 776. | CH | C(OMe) | OCH₂-(1-CH₃-cycPr) |
| 777. | CH | C(OMe) | OCH₂-cycBu |
| 778. | CH | C(OMe) | OCH₂-(1-CH₃-cycBu) |
| 779. | CH | C(OMe) | OCH₂-Phenyl |
| 780. | CH | C(OMe) | OCH₂CH₂-cycPr |
| 781. | CH | C(OMe) | OCH₂CH=cycPr |
| 782. | —COCH2OC— | | C≡C-cycPr |
| 783. | —COCH2OC— | | C≡C-(1-CH₃-cycPr) |
| 784. | —COCH2OC— | | C≡C-iPr |
| 785. | —COCH2OC— | | C≡C-nPr |
| 786. | —COCH2OC— | | C≡C-Bu |

-continued

| Entry # | W | X | R² |
|---|---|---|---|
| 787. | | —COCH2OC— | C≡C-iBu |
| 788. | | —COCH2OC— | C≡C-tBu |
| 789. | | —COCH2OC— | C≡C-Et |
| 790. | | —COCH2OC— | C≡C-Me |
| 791. | | —COCH2OC— | C≡C-Ph |
| 792. | | —COCH2OC— | C≡C-2-Pyridyl |
| 793. | | —COCH2OC— | C≡C-3-Pyridyl |
| 794. | | —COCH2OC— | C≡C-4-Pyridyl |
| 795. | | —COCH2OC— | C≡C-2-furanyl |
| 796. | | —COCH2OC— | C≡C-3-furanyl |
| 797. | | —COCH2OC— | C≡C-2-thienyl |
| 798. | | —COCH2OC— | C≡C-3-thienyl |
| 799. | | —COCH2OC— | CH=CH-cycPr |
| 800. | | —COCH2OC— | CH=CH-iPr |
| 801. | | —COCH2OC— | CH=CH-nPr |
| 802. | | —COCH2OC— | CH=CH-Bu |
| 803. | | —COCH2OC— | CH=CH-iBu |
| 804. | | —COCH2OC— | CH=CH-tBu |
| 805. | | —COCH2OC— | CH=CH-Et |
| 806. | | —COCH2OC— | CH=CH-Me |
| 807. | | —COCH2OC— | CH=CH-Ph |
| 808. | | —COCH2OC— | CH=CH-2-Pyridyl |
| 809. | | —COCH2OC— | CH=CH-3-Pyridyl |
| 810. | | —COCH2OC— | CH=CH-4-Pyndyl |
| 811. | | —COCH2OC— | CH=CH-2-furanyl |
| 812. | | —COCH2OC— | CH=CH-3-furanyl |
| 813. | | —COCH2OC— | CH=CH-2-thienyl |
| 814. | | —COCH2OC— | CH=CH-3-thienyl |
| 815. | | —COCH2OC— | $CH_2CH_2CH_2CH_2CH_3$ |
| 816. | | —COCH2OC— | $CH_2CH_2CH(CH_3)_2$ |
| 817. | | —COCH2OC— | $CH_2CH_2CH_2CH_3$ |
| 818. | | —COCH2OC— | $CH_2CH_2CH_3$ |
| 819. | | —COCH2OC— | $CH_2CH_2$-cycPr |
| 820. | | —COCH2OC— | $CH_2CH_2$-(1-$CH_3$-cycPr) |
| 821. | | —COCH2OC— | $CH_2CH_2$-tBu |
| 822. | | —COCH2OC— | $CH_2CH_2$-cycBu |
| 823. | | —COCH2OC— | $CH_2CH_2$-(1-$CH_3$-cycBu) |
| 824. | | —COCH2OC— | $CH_2CH_2$-2-Pyridyl |
| 825. | | —COCH2OC— | $CH_2CH_2$-3-Pyridyl |
| 826. | | —COCH2OC— | $CH_2CH_2$-4-Pyridyl |
| 827. | | —COCH2OC— | $CH_2CH_2$-2-furanyl |
| 828. | | —COCH2OC— | $CH_2CH_2$-3-furanyl |
| 829. | | —COCH2OC— | $CH_2CH_2$-2-thienyl |
| 830. | | —COCH2OC— | $CH_2CH_2$-3-thienyl |
| 831. | | —COCH2OC— | $CH_2C≡C$-cycPr |
| 832. | | —COCH2OC— | $CH_2C≡C$-2-furanyl |
| 833. | | —COCH2OC— | $CH_2CH=CH$-cycPr |
| 834. | | —COCH2OC— | $CH_2CH=CH$-2-furanyl |
| 835. | | —COCH2OC— | $CH=CHCH_2$-cycPr |
| 836. | | —COCH2OC— | $CH=CHCH_2$-2-furanyl |
| 837. | | —COCH2OC— | $OCH_2C≡C(CH_3)_2$ |
| 838. | | —COCH2OC— | E-$OCH_2C=CHCH_3$ |
| 839. | | —COCH2OC— | Z-$OCH_2C=CHCH_3$ |
| 840. | | —COCH2OC— | $OCH_2CH_3$ |
| 841. | | —COCH2OC— | $OCH_2CH_2CH_3$ |
| 842. | | —COCH2OC— | $OCH_2C=C(Cl)_2$ |
| 843. | | —COCH2OC— | $OCH_2C=CH_2$ |
| 844. | | —COCH2OC— | $OCH_2C≡CCH_3$ |
| 845. | | —COCH2OC— | $OCH_2CH_2CH_3$ |
| 846. | | —COCH2OC— | $OCH_2$-cycPr |
| 847. | | —COCH2OC— | $OCH_2$-(1-$CH_3$-cycPr) |
| 848. | | —COCH2OC— | $OCH_2$-cycBu |
| 849. | | —COCH2OC— | OCH2-(1-$CH_3$-cycBu) |
| 850. | | —COCH2OC— | $OCH_2$-Phenyl |
| 851. | | —COCH2OC— | $OCH_2CH_2$-cycPr |
| 852. | | —COCH2OC— | $OCH_2CH$=cycPr |

Utility

The compounds of this invention possess reverse transcriptase inhibitory activity, in particular, HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and In Vitro RNA Transcripts:

Plasmid PDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCT-TGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCT-TACTTTGATAAAACCTC 3') was complementary to nucleotides 2403–2425 of HXB2. The gag reporter probe (5' CCCAGTATTTGTCTACAGCCTTCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 µM stocks in 2×SSC (0.3 M NaCl, 0.03 M sodium citrate), 0.05 M Tris pH 8.8, 1 mg/mL BSA. The biotinylated capture probes were prepared as 100 µM stocks in water.

Streptavidin Coated Plates:

Streptavidin coated plates were obtained from Du Pont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 µg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were 1–3×$10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at 5×$10^5$ cells/mL in RPMI 1640, 5% FCS for bulk infections or at 2×$10^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline (PBS), 0.05% Tween 20.) A second hybridization of reporter probe to the immobilized complex of capture probe and hybridized target RNA was carried out in the washed streptavidin coated well by addition of 120 µl of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer δ(2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of 5×$10^5$ per mL (1×$10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 µg/mL. $IC_{90}$ values of other antiviral compounds, both more and less potent than ddC, were reproducible using several stocks of HIV-1 (RF) when this procedure was followed. This concentration of virus corresponded to ~3×$10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of PDAB 72 in vitro RNA transcript. The $IC_{90}$ for ddC, determined in each assay run, should be between 0.1 and 0.3 µg/mL. Finally, the plateau level of viral RNA produced by an effective reverse transcriptase inhibitor should be less than 10% of the level achieved in an uninhibited infection.

For antiviral potency tests, all manipulations in microtiter plates, following the initial addition of 2× concentrated compound solution to a single row of wells, were performed using a Perkin Elmer/Cetus ProPette.

Compounds tested in the above assay are considered to be active if they exhibit an $IC_{90}$ of $\leq 20$ μM. Preferred compounds of the present invention have $IC_{90}$'s of $\leq 5$ μM. More preferred compounds of the present invention have $IC_{90}$'s of $\leq 0.5$ μM. Even more preferred compounds of the present invention have $IC_{90}$'s of $\leq 0.05$ μM. Still more preferred compounds of the present invention have $IC_{90}$'s of $\leq 0.005$ μM.

Using the methodology described above, a number of compounds of the present invention were found to exhibit an $IC_{90}$ of $\leq 20$ μM, thereby confirming the utility of the compounds of the present invention as effective HIV inhibitors.

Protein Binding and Mutant Resistance

In order to characterize NNRTI analogs for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed is:
1. A compound of formula I:

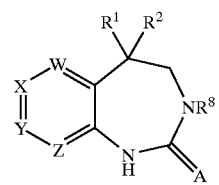

or a stereoisomer or pharmaceutically acceptable salt form thereof, wherein:
A is N—CN, NCONH$_2$, or N—OR$^{11}$;
W is N or CR$^3$;
X is N or CR$^{3a}$;
Y is N or CR$^{3b}$;
Z is N or CR$^{3c}$;
provided that if two of W, X, Y, and Z are N, then the remaining are other than N;
R$^1$ is selected from the group C$_{1-3}$ alkyl substituted with 0–7 halogen and cyclopropyl;
R$^2$ is selected from the group —R$^{2c}$, —OR$^{2c}$, —OCH$_2$R$^{2b}$, —OCH$_2$CH$_2$R$^{2b}$, —OCH$_2$C H=CH—R$^{2b}$, —OCH$_2$C≡C—R$^{2b}$, —SR$^{2c}$, —SCH$_2$R$^{2b}$, —SCH$_2$CH$_2$R$^{2b}$, —SCH$_2$C H=CH—R$^{2b}$, and —SCH$_2$C≡C—R$^{2b}$;
R$^{2a}$ is selected from the group H, CH$_3$, CH$_2$CH$_3$, CH(CH$_3$)$_2$, and CH$_2$CH$_2$CH$_3$;
R$^{2b}$ is H or R$^{2c}$;

R$^{2c}$ is selected from the group C$_{1-6}$ alkyl substituted with 0–2 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, phenyl substituted with 0–2 R$^{3d}$, and 3–6 membered heterocyclic group containing 1–3 heteroatoms selected from the group O, N, and S, substituted with 0–2 R$^{3d}$;
alternatively, the group —NR$^{2a}$R$^{2c}$ represents a 4–7 membered cyclic amine, wherein 0–1 carbon atoms are replaced by O or NR$^5$;
R$^3$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;
R$^{3a}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;
alternatively, R$^3$ and R$^{3a}$ together form —OCH$_2$O—;
R$^{3b}$, at each occurrence, is independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;
alternatively, R$^{3a}$ and R$^{3b}$ together form —OCH$_2$O—;
R$^{3c}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;
alternatively, R$^{3b}$ and R$^{3c}$ together form —OCH$_2$O—;
R$^{3d}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;
R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;
R$^{3f}$, at each occurrence, is independently selected from the group C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;
R$^{3g}$, at each occurrence, is independently selected from the group C$_{1-4}$ alkyl, C$_{2-5}$ alkenyl, —OH, C$_{1-4}$ alkoxy, OCF$_3$, F, Cl, Br, I, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, C$_{3-10}$ carbocycle substituted with 0–3 R$^{3f}$ and a 5–10 membered heterocyclic group containing 1–3 heteroatoms selected from the group O, N, and S, substituted with 0–3 R$^{3f}$; and,
R$^4$ is selected from the group F, Cl, Br, I, C$_{1-6}$ alkyl substituted with 0–2 R$^{3e}$, C$_{3-10}$ carbocycle substituted with 0–2 R$^{3e}$, phenyl substituted with 0–5 R$^{3e}$, and a 5–10 membered heterocyclic group containing 1–3 heteroatoms selected from the group O, N, and S, substituted with 0–2 R$^{3e}$;
R$^5$ and R$^{5a}$ at each occurrence are independently selected from the group H and C$_{1-4}$ alkyl;
alternatively, R$^5$ and R$^{5a}$, together with the nitrogen to which they are attached, combine to form a 5–6 membered ring containing 0–1 O or N atoms;

$R^6$ is selected from the group H, OH, $C_{1-4}$ alkyl, $C_{1-4}$ alkoxy, and $NR^5R^{5a}$;

$R^7$ is selected from the group $C_{1-3}$ alkyl and $C_{1-3}$ alkoxy;

$R^8$ is selected from the group H, $OR^9$, $SR^9$, $NR^5R^9$, $C_{1-6}$ alkyl substituted with 0–3 $R^{3g}$, $C_{2-6}$ alkenyl substituted with 0–3 $R^{3g}$, $C_{2-6}$ alkynyl substituted with 0–3 $R^{3g}$, $C_{3-5}$ cycloalkyl substituted with 0–2 $R^{3f}$, phenyl substituted with 0–5 $R^{3f}$, and a 5–6 membered heterocyclic group containing 1–3 heteroatoms selected from the group O, N, and S, substituted with 0–2 $R^{3f}$;

$R^9$ is selected from the group $C_{3-10}$ carbocycle substituted with 0–5 $R^{3f}$ and a 5–10 membered heterocyclic group containing 1–3 heteroatoms selected from the group O, N, and S, substituted with 0–2 $R^{3f}$;

$R^{10}$ is selected from the group $C_{1-4}$ alkyl and phenyl; and $R^{11}$ is selected from the group H and $C_{1-4}$ alkyl.

2. A compound according to claim 1, wherein:

$R^1$ is selected from the group $C_{1-3}$ alkyl substituted with 1–7 halogen and cyclopropyl;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group $C_{1-5}$ alkyl substituted with 0–2 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, and phenyl substituted with 0–2 $R^{3d}$;

$R^3$, at each occurrence, is independently selected from the group H, $C_{1-4}$ alkyl, OH, $C_{1-4}$ alkoxy, F, Cl, Br, I, $NR^5R^{5a}$, $NO_2$, —CN, $C(O)R^6$, $NHC(O)R^7$, $NHC(O)NR^5R^{5a}$, and a 5–6 membered heteroaromatic ring containing 1–4 heteroatoms selected from the group O, N, and S;

$R^{3a}$, at each occurrence, is independently selected from the group H, $C_{1-4}$ alkyl, OH, $C_{1-4}$ alkoxy, F, Cl, Br, I, $NR^5R^{5a}$, $NO_2$, —CN, $C(O)R^6$, $NHC(O)R^7$, $NHC(O)NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$, at each occurrence, is independently selected from the group H, $C_{1-4}$ alkyl, OH, $C_{1-4}$ alkoxy, F, Cl, Br, I, $NR^5R^{5a}$, $NO_2$, —CN, $C(O)R^6$, $NHC(O)R^7$, and $NHC(O)NR^5R^{5a}$;

alternatively, $R^{3a}$ and $R^{3b}$ together form —$OCH_2O$—;

$R^4$ is selected from the group Cl, F, $C_{1-4}$ alkyl substituted with 0–2 $R^{3e}$, $C_{3-5}$ carbocycle substituted with 0–2 $R^{3e}$, phenyl substituted with 0–5 $R^{3e}$, and a 5–6 membered heterocyclic group containing 1–3 heteroatoms selected from the group O, N, and S, substituted with 0–2 $R^{3e}$;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $CH(CH_3)_2$, $OCH_3$, $OC_2H_5$, and $OCH(CH_3)_2$; and, $R^8$ is selected from the group H, cyclopropyl, $CH_3$, $C_2H_5$, and $CH(CH_3)_2$.

3. A compound according to claim 2, wherein:

$R^1$ is selected from the group $CF_3$, $C_2F_5$, and cyclopropyl;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group $C_{1-3}$ alkyl substituted with 0–2 $R^4$, $C_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$;

$R^3$, at each occurrence, is independently selected from the group H, $C_{1-3}$ alkyl, OH, $C_{1-3}$ alkoxy, F, Cl, Br, I, $NR^5R^{5a}$, $NO_2$, —CN, $C(O)R^6$, $NHC(O)R^7$, and $NHC(O)NR^5R^{5a}$;

alternatively, $R^3$ and $R^{3a}$ together form —$OCH_2O$—;

$R^{3b}$ is H;

$R^{3c}$ is H;

$R^{3e}$, at each occurrence, is independently selected from the group H, $C_{1-4}$ alkyl, —OH, $C_{1-4}$ alkoxy, $OCF_3$, F, Cl, —$NR^5R^{5a}$, —$C(O)R^6$, and —$SO_2NR^5R^{5a}$;

$R^4$ is selected from the group Cl, F, $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic group containing 1–3 heteroatoms selected from the group O, N, and S, substituted with 0–1 $R^{3e}$;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$; and, $R^8$ is selected from the group H, cyclopropyl, $CH_3$, and $C_2H_5$.

4. A compound according to claim 3, wherein:

$R^1$ is $CF_3$;

$R^2$ is selected from the group —$R^{2c}$, —$OR^{2c}$, —$OCH_2R^{2b}$, —$OCH_2CH_2R^{2b}$, —$OCH_2CH=CH$—$R^{2b}$, —$OCH_2C\equiv C$—$R^{2b}$, —$SR^{2c}$, —$SCH_2R^{2b}$, —$SCH_2CH_2R^{2b}$, —$SCH_2CH=CH$—$R^{2b}$, and —$SCH_2C\equiv C$—$R^{2b}$;

$R^{2b}$ is H or $R^{2c}$;

$R^{2c}$ is selected from the group methyl substituted with 0–2 $R^4$, ethyl substituted with 0–2 $R^4$, propyl substituted with 0–2 $R^4$, ethenyl substituted with 0–2 $R^4$, 1-propenyl substituted with 0–1 $R^4$, 2-propenyl substituted with 0–1 $R^4$, ethynyl substituted with 0–1 $R^4$, 1-propynyl substituted with 0–1 $R^4$, 2-propynyl substituted with 0–1 $R^4$, and cyclopropyl substituted with 0–1 $R^{3d}$;

$R^3$, at each occurrence, is independently selected from the group H, $C_{1-3}$ alkyl, OH, $C_{1-3}$ alkoxy, F, Cl, $NR^5R^{5a}$, $NO_2$, —CN, and $C(O)R^6$;

alternatively, $R^3$ and $R^{3a}$ together form —$OCH_2O$—;

$R^{3d}$, at each occurrence, is independently selected from the group $CH_3$, —OH, $OCH_3$, $OCF_3$, F, Cl, and —$NR^5R^{5a}$;

$R^{3e}$, at each occurrence, is independently selected from the group $CH_3$, —OH, $OCH_3$, $OCF_3$, F, Cl, and —$NR^5R^{5a}$;

$R^4$ is selected from the group Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic group containing 1–3 heteroatoms selected from the group O, N, and S, substituted with 0–1 $R^{3e}$, wherein the heterocyclic group is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$; and, $R^8$ is selected from the group H, cyclopropyl, and $C_2H_5$.

5. A compound according to claim 4, wherein the compound is of formula Ia

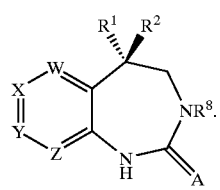

Ia

6. A compound according to claim 4, wherein the compound is of formula Ib:

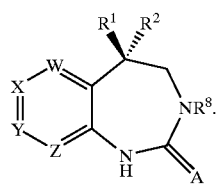

Ib

7. A compound according to claim 1, wherein the compound is selected from the group:
   7-chloro-2-cyanoimino-5-(cyclopropylmethyloxy)-1,5-dihydro-5-trifluoromethyl-1,3-benzodiazepine;
   7-chloro-2-cyanoimino-5-(cyclobutylmethyloxy)-1,5-dihydro-5-trifluoromethyl-1,3-benzodiazepine;
   7-chloro-2-cyanoimino-5-(cyclopropylmethyloxy)-1,5-dihydro-3-ethyl-5-trifluoromethyl-1,3-benzodiazepine;
   7-chloro-5-cyclopropylmethyloxy-1,5-dihydro-2-methoxyimino-5-trifluoromethyl-1,3benzodiazepine;
   7-chloro-5-cyclopropylmethyloxy-1,5-dihydro-3-ethyl-2-methoxyimino-5-trifluoromethyl-1,3-benzodiazepine;
   or a pharmaceutically acceptable salt form thereof.

8. A compound according to claim 1, wherein the compound is selected from the group:
   (S)-7-chloro-2-cyanoimino-5-(cyclopropylmethyloxy)-1,5-dihydro-5-trifluoromethyl-1,3-benzodiazepine;
   (S)-7-chloro-2-cyanoimino-5-(cyclobutylmethyloxy)-1,5-dihydro-5-trifluoromethyl-1,3-benzodiazepine;
   (S)-7-chloro-2-cyanoimino-5-(cyclopropylmethyloxy)-1,5-dihydro-3-ethyl-5-trifluoromethyl-1,3-benzodiazepine;
   (S)-7-chloro-5-cyclopropylmethyloxy-1,5-dihydro-2-methoxyimino-5-trifluoromethyl-1,3-benzodiazepine;
   (S)-7-chloro-5-cyclopropylmethyloxy-1,5-dihydro-3-ethyl-2-methoxyimino-5-trifluoromethyl-1,3-benzodiazepine;
   or a pharmaceutically acceptable salt form thereof.

9. A compound according to claim 1, wherein the compound is selected from the group:
   (R)-7-chloro-2-cyanoimino-5-(cyclopropylmethyloxy)-1,5-dihydro-5-trifluoromethyl-1,3-benzodiazepine;
   (R)-7-chloro-2-cyanoimino-5-(cyclobutylmethyloxy)-1,5-dihydro-5-trifluoromethyl-1,3-benzodiazepine;
   (R)-7-chloro-2-cyanoimino-5-(cyclopropylmethyloxy)-1,5-dihydro-3-ethyl-5-trifluoromethyl-1,3-benzodiazepine;
   (R)-7-chloro-5-cyclopropylmethyloxy-1,5-dihydro-2-methoxyimino-5-trifluoromethyl-1,3-benzodiazepine;
   (R)-7-chloro-5-cyclopropylmethyloxy-1,5-dihydro-3-ethyl-2-methoxyimino-5-trifluoromethyl-1,3-benzodiazepine;
   or a pharmaceutically acceptable salt form thereof.

10. A pharmaceutical composition comprising a pharmaceutically acceptable carrier and a therapeutically effective amount of a compound according to claim 1 or pharmaceutically acceptable salt form thereof.

11. A method of treating HIV infection which comprises administering to a host in need of such treatment a therapeutically effective amount of a compound according to claim 1 or pharmaceutically acceptable salt form thereof.

* * * * *

UNITED STATES PATENT AND TRADEMARK OFFICE
CERTIFICATE OF CORRECTION

PATENT NO. : 7,015,214 B2
APPLICATION NO. : 10/108842
DATED : March 21, 2006
INVENTOR(S) : Donna M. Bilder It is certified that error appears in the above-identified patent and that said Letters Patent is hereby corrected as shown below:

Column 53, Starting at Line 60

"$R^2$ is selected from the group $-R^{2c}$, $-OR^{2c}$, $-OCH_2R^{2b}$, $-OCH_2CH_2R^{2b}$, $-OCH_2C\underline{H}=CH-R^{2b}$, $-OCH_2C\equiv C-R^{2b}$, $-SR^{2c}$, $-SCH_2R^{2b}$, $-SCH_2CH_2R^{2b}$, $-SCH_2C\underline{H}=CH-R^{2b}$, and $-SCH_2C\equiv C-R^{2b}$;"

should read

--$R^2$ is selected from the group $-R^{2c}$, $-OR^{2c}$, $-OCH_2R^{2b}$, $-OCH_2CH_2R^{2b}$, $-OCH_2CH=CH-R^{2b}$, $-OCH_2C\equiv C-R^{2b}$, $-SR^{2c}$, $-SCH_2R^{2b}$, $-SCH_2CH_2R^{2b}$ $-SCH_2CH=CH-R^{2b}$, and $-SCH_2C\equiv C-R^{2b}$;--

Column 56, Starting at Line 31

"$R^2$ is selected from the group $-R^{2c}$, $-OR^{2c}$, $-OCH^2R^{2b}$, $-OCH_2CH_2R^{2b}$ $-OCH_2C\underline{H}=CH-R^{2b}$, $-OCH_2C\equiv C-R^{2b}$, $-SR^{2c}$, $-SCH_2R^{2b}$, $-SCH_2CH_2R^{2b}$, $-SCH_2C\underline{H}=CH-R^{2b}$, and $-SCH_2C\equiv C-R^{2b}$;"

UNITED STATES PATENT AND TRADEMARK OFFICE
CERTIFICATE OF CORRECTION

PATENT NO. : 7,015,214 B2
APPLICATION NO. : 10/108842
DATED : March 21, 2006
INVENTOR(S) : Donna M. Bilder It is certified that error appears in the above-identified patent and that said Letters Patent is hereby corrected as shown below:

should read

--$R^2$ is selected from the group $-R^{2c}$, $-OR^{2c}$, $-OCH_2R^{2b}$, $-OCH_2CH_2R^{2b}$ $-OCH_2CH=CH-R^{2b}$, $-OCH_2C{\equiv}C-R^{2b}$, $-SR^{2c}$, $-SCH_2R^{2b}$, $-SCH_2CH_2R^{2b}$ $-SCH_2CH=CH-R^{2b}$, and $-SCH_2C{\equiv}C-R^{2b}$;--

Signed and Sealed this

Twenty-fourth Day of October, 2006

JON W. DUDAS
*Director of the United States Patent and Trademark Office*